(12) United States Patent
Schmidt et al.

(10) Patent No.: US 7,683,232 B2
(45) Date of Patent: Mar. 23, 2010

(54) PRODUCTION OF OLEFINS HAVING A FUNCTIONAL GROUP

(75) Inventors: Lanny D. Schmidt, Minneapolis, MN (US); Ramanathan Subramanian, Minneapolis, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 1206 days.

(21) Appl. No.: 11/137,770

(22) Filed: May 25, 2005

(65) Prior Publication Data

US 2006/0014840 A1 Jan. 19, 2006

Related U.S. Application Data

(60) Provisional application No. 60/574,381, filed on May 25, 2004.

(51) Int. Cl.
C07C 5/333 (2006.01)
C07C 45/00 (2006.01)

(52) U.S. Cl. .................. 585/660; 585/627; 585/629; 585/658; 568/320; 518/703; 423/648.1

(58) Field of Classification Search .................. 585/624, 585/627, 629, 658, 669, 613; 252/373, 376; 423/648.1; 518/703; 568/320; 549/248
See application file for complete search history.

(56) References Cited

U.S. PATENT DOCUMENTS

| | | | | |
|---|---|---|---|---|
| 2,530,923 A | * | 11/1950 | Turk et al. | 554/115 |
| 3,502,739 A | * | 3/1970 | Begley et al. | 585/624 |
| 3,547,984 A | * | 12/1970 | Young | 560/241 |
| 3,686,287 A | * | 8/1972 | Knights | 560/245 |
| 3,900,646 A | | 8/1975 | Clyde | |
| 3,957,685 A | | 5/1976 | Heide et al. | |
| 3,998,758 A | | 12/1976 | Clyde | |
| 4,088,607 A | | 5/1978 | Weidenbach et al. | |
| 4,251,239 A | | 2/1981 | Clyde et al. | |
| 4,253,302 A | | 3/1981 | Asano et al. | |
| 4,308,233 A | | 12/1981 | Narumiya et al. | |
| 4,568,595 A | | 2/1986 | Morris | |

(Continued)

FOREIGN PATENT DOCUMENTS

CA 2 323 728 A1 4/2001

(Continued)

OTHER PUBLICATIONS

ASTM Standard D 6751-06$^{e1}$, Standard Specification for Biodiesel Fuel (B100) Blend Stock for Middle Distillate Fuels, ASTM International, *Annual Book of Standards*, Book of Standards vol. 05.04, May 2006 (7 pages).

(Continued)

*Primary Examiner*—Porfirio Nazario-Gonzalez
*Assistant Examiner*—Yate' K Cutliff
(74) *Attorney, Agent, or Firm*—Mueting, Raasch & Gebhardt, P.A.

(57) ABSTRACT

A process is disclosed for producing functionalized olefins from a fuel source including an organic compound including a functional group. Useful fuel sources include, for example, biofeedstocks (e.g., carbohydrates, triglycerides, polyols, and biodiesel). The process is preferably carried out by partial oxidation. The overall process can be carried out autothermally.

60 Claims, 7 Drawing Sheets

U.S. PATENT DOCUMENTS

| | | |
|---|---|---|
| 4,810,685 A | 3/1989 | Twigg et al. |
| 4,863,712 A | 9/1989 | Twigg et al. |
| 4,865,820 A | 9/1989 | Dunster et al. |
| 4,940,826 A | 7/1990 | Freide et al. |
| 5,105,052 A | 4/1992 | Freide et al. |
| 5,221,464 A | 6/1993 | Durante et al. |
| 5,382,741 A | 1/1995 | Astbury et al. |
| 5,500,149 A | 3/1996 | Green et al. |
| 5,593,935 A | 1/1997 | Golunski et al. |
| 5,597,771 A | 1/1997 | Hu et al. |
| 5,639,929 A * | 6/1997 | Bharadwaj et al. .......... 585/658 |
| 5,648,582 A | 7/1997 | Schmidt et al. |
| 5,654,491 A | 8/1997 | Goetsch et al. |
| 5,856,585 A | 1/1999 | Sanfilippo et al. |
| 5,905,180 A | 5/1999 | Yokoyama et al. |
| 5,980,731 A | 11/1999 | Kao et al. |
| 5,980,782 A | 11/1999 | Hershkowitz et al. |
| 5,993,192 A | 11/1999 | Schmidt et al. |
| 6,072,097 A | 6/2000 | Yokoyama et al. |
| 6,083,425 A | 7/2000 | Clawson et al. |
| 6,092,921 A | 7/2000 | Wentinck et al. |
| 6,123,913 A | 9/2000 | Clawson et al. |
| 6,126,908 A | 10/2000 | Clawson et al. |
| 6,197,717 B1 | 3/2001 | Alexander et al. |
| 6,207,122 B1 | 3/2001 | Clawson et al. |
| 6,221,280 B1 | 4/2001 | Anumakonda et al. |
| 6,245,303 B1 | 6/2001 | Bentley et al. |
| 6,254,807 B1 * | 7/2001 | Schmidt et al. ............. 252/373 |
| 6,254,839 B1 | 7/2001 | Clawson et al. |
| 6,365,543 B1 | 4/2002 | Schmidt et al. |
| 6,387,554 B1 | 5/2002 | Verykios |
| 6,407,301 B1 | 6/2002 | Foley et al. |
| 6,436,363 B1 | 8/2002 | Hwang et al. |
| 6,444,867 B1 | 9/2002 | Samsel et al. |
| 6,452,061 B1 | 9/2002 | Schmidt et al. |
| 6,455,597 B2 | 9/2002 | Hohn et al. |
| 6,468,480 B1 | 10/2002 | Clawson et al. |
| 6,506,359 B1 | 1/2003 | Maruko |
| 6,548,447 B1 | 4/2003 | Yokoyama et al. |
| 6,605,376 B2 | 8/2003 | Verykios |
| 6,641,625 B1 | 11/2003 | Clawson et al. |
| 6,783,742 B2 | 8/2004 | Bentley et al. |
| 6,846,773 B1 | 1/2005 | Yokoyama et al. |
| 6,911,187 B2 | 6/2005 | Maruko |
| 6,986,797 B1 | 1/2006 | Clawson et al. |
| 7,033,407 B2 | 4/2006 | Maruko |
| 7,066,973 B1 | 6/2006 | Bentley et al. |
| 7,083,775 B2 | 8/2006 | Wieland et al. |
| 2001/0009653 A1 | 7/2001 | Clawson et al. |
| 2001/0023034 A1 | 9/2001 | Verykios |
| 2001/0027258 A1 | 10/2001 | Hohn et al. |
| 2002/0000066 A1 | 1/2002 | Bentley et al. |
| 2002/0009408 A1 | 1/2002 | Wieland et al. |
| 2002/0087042 A1 | 7/2002 | Schmidt et al. |
| 2003/0041519 A1 | 3/2003 | Maruko |
| 2003/0060364 A1 | 3/2003 | Anzai et al. |
| 2003/0074839 A1 | 4/2003 | Maruko |
| 2004/0014600 A1 | 1/2004 | Fukunaga |
| 2004/0199038 A1 | 10/2004 | Schmidt et al. |
| 2005/0178064 A1 | 8/2005 | Maruko |
| 2005/0260123 A1 | 11/2005 | Deluga et al. |

FOREIGN PATENT DOCUMENTS

| | | |
|---|---|---|
| EP | 0 303 439 B1 | 10/1992 |
| EP | 0 576 096 A2 | 12/1993 |
| EP | 0 640 559 A1 | 3/1995 |
| EP | 1 043 271 A1 | 10/2000 |
| EP | 0 922 011 B1 | 7/2001 |
| EP | 1 118 583 A2 | 7/2001 |
| EP | 1 109 876 B1 | 7/2003 |
| EP | 1 007 472 B1 | 9/2003 |
| FR | 1379027 | 11/1964 |
| GB | 1067957 | 5/1967 |
| JP | 2001-080904 | 3/2001 |
| JP | 2001-089108 | 4/2001 |
| WO | WO 96/13475 A1 | 5/1996 |
| WO | WO 96/33149 A1 | 10/1996 |
| WO | WO 97/26987 A1 | 7/1997 |
| WO | WO 97/29062 A1 | 8/1997 |
| WO | WO 98/08771 A2 | 3/1998 |
| WO | WO 98/08771 A3 | 3/1998 |
| WO | WO 99/35082 A1 | 7/1999 |
| WO | WO 99/36351 A1 | 7/1999 |
| WO | WO 99/61369 A1 | 12/1999 |
| WO | WO 00/14180 A1 | 3/2000 |
| WO | WO 00/66487 A1 | 11/2000 |
| WO | WO 01/32556 A1 | 5/2001 |
| WO | WO 01/64577 A1 | 9/2001 |
| WO | WO 2004/044095 A2 | 5/2004 |
| WO | WO 2004/044095 A3 | 5/2004 |

OTHER PUBLICATIONS

ASTM Standard D6751-03 Standard Specification for Biodiesel Fuel (B100) Blend Stock for Distillate Fuels, ASTM International, *Annual Book of Standards*, Book of Standards vol. 05.04, Jul. 2003 (6 pages).

Aupretre et al., "Le vaporeformage catalytique: Application a la production embarquee d'hydrogene a partir d'hydrocarbures ou d'alcools," *Ann. Chim. Sci. Mat.*, 2001, 26(4):93-106 (with English language abstract).

Beal, "News: Team engineers hydrogen from biomass" [online]. University of Wisconsin-Madison, Aug. 28, 2008 [retrieved on Oct. 24, 2005]. Retrieved from the Internet:<URL:http:www.news.wisc.edu/story.php?get=7766>; 2 pgs.

Beretta et al., "Production of Olefins via Oxidative Dehydrogenation of Propane in Autothermal Conditions," *J. Catal.*, Jun. 1999; 184(2):469-478.

Biodiesel Definitions, Biodiesel.org—Biodiesel 101 [online]. [retrieved on Nov. 1, 2006]. Retrieved from the Internet:<URL: http://biodiesel.org/resources/definitions/default.shtm.>; 2 pgs.

Biodiesel Emissions Compared to Conventional Diesel [online]. [retrieved on Jan. 11, 2006 ]. Retrieved from the Internet: <URL: www.soypower.net/BiodieselEmissions.asp.>; West Central, Ralston, IA, 2 pgs.

Bodke et al., "The Effect of Ceramic Supports on Partial Oxidation of Hydrocarbons Over Noble Metal Coated Monoliths," *J. Catal.*, 1998; 179:138-149.

Bodke et al., "High Selectivities to Ethylene by Partial Oxidation of Ethane," *Science*, 1999; 285:712-715.

Bodke et al., "Oxidative Dehydrogenation of Ethane at Millisecond Contact Times: Effect of $H_2$ Addition," *J. Catal.*, 2000; 191:62-74.

Brown, "A comparative study of fuels for on-board hydrogen production for fuel-cell-powered automobiles," *Int. J. Hydrogen Energy*, 2001, 26:381-397.

Burch et al., "Investigation of the reactions of acetaldehyde on promoted rhodium catalysts," *Applied Cataylsis A: General*, 1992; 88:61-76.

Cavallaro et al., "Ethanol steam reforming in a molten carbonate fuel cell. A preliminary kinetic investigation," *Int. J. Hydrogen Energy*, 1996; 21(6):465-469.

Cavallaro, "Ethanol Steam Reforming on $Rh/Al_2O_3$ Catalysts," *Energy & Fuels*, 2000, 14:1195-1199.

Chomet et al., "Harnessing hydrogen," *Nature*, Aug. 29, 2002; 418:928-929.

Cohn et al., "Onboard plasmatron generation of hydrogen for extremely low emission vehicles with internal combustion engines," *Int. J. of Vehicle Design*, 1996; 17(5/6):550-561.

Cordi et al., "Transient oxidation of volatile organic compounds on a $CuO/Al_2O_3$ catalyst," *Applied Catalysis B: Environmental*, 1997; 14:23-36.

Cortright et al., "Hydrogen from catalytic reforming of biomass-derived hydrocarbons in liquid water," *Nature*, Aug. 29, 2002; 418:964-967.

Czernik et al., "Hydrogen by Catalytic Steam Reforming of Liquid Byproducts from Biomass Thermoconversion Processes," *Ind. Eng. Chem. Res.*, 2002; 41(17):4209-4215.

Deluga et al., "Renewable Hydrogen from Ethanol by Autothermal Reforming," *Science*, Feb. 2004; 303:993-997.

Demirbaş, "Chemical and Fuel Properties of Seventeen Vegetable Oils," *Energy Sources*, Jul. 2003; 25(7):721-728.

Deng et al., "Downer Catalytic Pyrolysis (DCP): A Novel Process for Light Olefins Production," *Chem. Eng. Technol*, 2002; 25:711-716.

Dietz III et al., "Partial Oxidation of $C_5$ and $C_6$ Alkanes over Monolith Catalysts at Short Contact Times," *J. Catal.*, 1996; 176:459-473.

Fatsikostas et al., "Steam reforming of biomass-derived ethanol for the production of hydrogen for fuel cell applications," *Chem. Commun.*, 2001; 851-852.

Fishtik et al., "A thermodynamic analysis of hydrogen production by steam reforming of ethanol via response reactions," *Int. J. Hydrogen Energy*, 2000; 25:31-45.

Freni, "Rh based catalysts for indirect internal reforming ethanol applications in molten carbonate fuel cells," *J. Power Sources*, 2001; 94:14-19.

Galvita et al., "Synthesis gas production by steam reforming of ethanol," *Applied Catalysis A: General*, 2001; 220:123-127.

Goetsch et al., "Microsecond Catalytic Partial Oxidation of Alkanes," *Science*, Mar. 1996; 271:1560-1562.

Gomez et al., "Kinetic Study of Partial Oxidation of Ethanol over VMgO Catalyst," *Ind. Eng. Chem. Res.*, 1997; 36:3468-3472.

Hacohen et al:, "Driving Cycle Simulation of a Vehicle Motored by a SI Engine Fueled with $H_2$-Enriched Gasoline," *Int. J. of Hydrogen Energy*, 1991; 16(10):695-702.

Henning et al., "Oxidative dehydrogenation of ethane at short contact times: species and temperature profiles within and after the catalyst," *Chem. Eng. Sci.*, 2002; 57(14):2615-2625.

Hickman et al., "Synthesis gas formation by direct oxidation of methane over Rh monoliths," *Catal. Lett.*, 1993; 17(3-4):223-237.

Hickman et al., "Production of Syngas by Direct Catalytic Oxidation of Methane," *Science*, Jan. 15, 1993; 259:343-346.

Hickman et al., "Steps in $CH_4$ Oxidation on Pt and Rh Surfaces: High-Temperature Reactor Simulations," *AIChE J.*, 1993; 39(7):1164-1177.

"Homogenous-Heterogeneous Combustion: Thermal and Chemical Coupling," Abstract, DOE Contract No. FG02-88ER13878, Jan. 1992, 2 pgs.

Huff et al., "Partial Oxidation of $CH_4$, $C_2H_6$, and $C_3H_8$ on Monoliths at Short Contact Times," *Stud, Surf. Sci. Catal.*, Natural Gas Conversion II, Proceedings of the Third Natural Gas Conversion Symposium, Sydney, Australia, Jul. 4-9, 1993; 81:315-320 (1994).

Ioannides, "Thermodynamic analysis of ethanol processors for fuel cell applications," *Power Sources*, 2001, 92:17-25.

Jamal et al., "On-Board Generation of Hydrogen-Rich Gaseous Fuels—A Review," *Int. J. Hydrogen Energy*, 1994; 19(7):557-572.

Klein et al., "Catalytic partial oxidation of methane to syngas: staged and stratified reactors with steam addition," *Stud. Surf. Sci. Catal.*, Natural Gas Conversion VI, Proceedings of the Sixth Natural Gas Conversion Symposium, Alaska, Jun. 17-22, 2001; 136:245-250 (2001).

Krummenacher et al., "Catalytic partial oxidation of higher hydrocarbons at millisecond contact times: decane, hexadecane, and diesel fuel," *J. Catal*, 2003; 215:332-343.

Krummenacher et al., "Catalytic Partial Oxidation of Higher Hydrocarbons at Millisecond Contact Times: Decane, Hexadecane, and Diesel Fuel," 18th North American Catalysis Society Meeting, Cancun, Mexico, Jun. 1-6, 2003; 2 pgs.

Lakshmi et al., "Synthesis, Characterization, and Activity Studies of Vanadia Supported on Zirconia and Phosphorus-Modified Zirconia," *Langmuir*, 1999; 15:3521-3528.

"Lightweight Valve Train Materials," Report based on research conducted under DOE Cooperative Agreement DE-FCO5-97OR22579, U.S. Dept. of Energy, Metals and Ceramics Division, Heavy Vehicle Propulsion Materials Program Quarterly Progress Report, Oak Ridge National Laboratory, Oak Ridge, TN (Jan.- Mar. 2005) 10 pages.

Mariño et al., "Hydrogen from steam reforming of ethanol. Characterization and performance of copper-nickel supported catalysts," *Int. J. Hydrogen Energy*, 1998; 23(12):1095-1101.

Mariño et al., "Hydrogen production from steam reforming of bioethanol using Cu/Ni/K/γ-$Al_2O_3$ catalysts. Effect of Ni," *Int. J. of Hydrogen Energy*, 2001, 26:665-668.

Mazzocchia et al., "Hydrogenation of CO over $ZrO_2$-supported Rh catalysts: kinetic aspects," *J. Molecular Catalysis*, 1990; 60:283-294.

Mazzocchia et al., "Hydrogenation of CO over Rh/$SiO_2$-$CeO_2$ catalysts: kinetic evidences," *J. Molecular Catalysis A: Chemical*, 2001; 165:219-230.

O'Connor et al., "High yields of synthesis gas by millisecond partial oxidation of higher hydrocarbons," *Catalysis Letters*, 2000; 70:99-107.

Otsuka et al., "The Partial Oxidation of Light Alkanes ($CH_4$, $C_2H_6$, $C_3H_8$) Over B-P Mixed Oxides," *Stud. Surf. Sci. Catal.*, Natural Gas Conversion, Proceedings of the Natural Gas Conversion Symposium, Oslo, Aug. 12-17, 1990; 61:15-23 (1991).

Pestryakov et al., "Physicochemical study of active sites of metal catalysts for alcohol partial oxidation," *Molecular Catalysis A: Chemical*, 2000; 158:325-329.

Rampe et al., "Hydrogen generation from biogenic and fossil fuels by autothermal reforming," *J. Power Sources*, 2000; 86:536-541.

Schmidt, "Startup and Transients in Millisecond Chemical Reactors," Grant Abstract, Grant No. CTS-0211860 [online]. National Science Foundation, project dates May 1, 2002 to Apr. 30, 2005 [retrieved on Jan. 11, 2006]. Retrieved from the Internet:<URL:www.nsf gov/awardsearch/showAward.do?AwardNumber=0211860.>; 2 pages.

Su et al., "Heterogeneous Partial Oxidation of Light Alkanes," Abstracts of Papers, 224th ACS National Meeting, Boston, MA, Aug. 18-22, 2002; 3 pgs.

Subramanian et al., "Renewable Olefins from Biodiesel by Autothermal Reforming," *Angew. Chem. Int. Ed.*, 2005; 44:302-305; on-line publication available Dec. 21, 2004.

Tamman et al., "Zur Rekristallisation von Metallen und Salzen," *Zeitschrift für Anorganische und Allgemeine Chemie*, 1923; 126:119-128.

Traxel et al., "Partial oxidation of methanol at millisecond contact times," *Applied Catalysis A: General*, 2003; 244:129-140.

Tsiakaras et al., "Thermodynamic analysis of a solid oxide fuel cell system fuelled by ethanol," *Power Sources,* 102:210-217 (2001).

Vasudeva et al., "Steam reforming of ethanol for hydrogen production: thermodynamic analysis," *Int. J. Hydrogen Energy*, 1996; 21(1):13-18.

Vickers et al., *PLOT Column Considerations for the Gas Chromatographic Analysis of Ozone Precursors*, J&W Scientific, Folsom, CA, Aug. 1998:9 pgs.

Wang et al., "Study on the partial oxidation of ethanol to hydrogen in the presence of Ni-Fe catalyst," *Acta Phys.—Chim. Sin.* (*Wuji Huaxue Xuebao*), 2002, 18(5):426-431; with English language abstract and translation, 18 pgs total.

Wheeler et al., "The water-gas-shift reaction at short contact times," *J. Catal.*, Apr. 2004; 223:191-199.

\* cited by examiner

PRODUCTION OF OLEFINS HAVING A FUNCTIONAL GROUP

CROSS-REFERENCE TO RELATED APPLICATIONS

The present application claims the benefit of U.S. Provisional Application No. 60/574,381, filed on 25 May 2004, which is incorporated herein by reference in its entirety.

STATEMENT OF GOVERNMENT RIGHTS

The present invention was made with support from the National Science Foundation, Grant No. CTS-0211860. The government may have certain rights in this invention.

BACKGROUND

Olefins are currently the largest volume chemical intermediates produced by the chemical industry, with a global annual production of over 300 billion pounds per year (Deng et al., *Chem. Eng. Technol.*, 25:711 (2002)). Currently olefins are produced almost exclusively from fuels such as ethane or other light alkanes, such as naphtha, in a process known as steam cracking. This process takes place by homogeneous pyrolysis, typically at approximately 800 degrees Celsius (° C.). For ethane this process is represented by the reaction:

$C_2H_6 \rightarrow C_2H_4 + H_2 \; \Delta H_R = +136 \text{ kJ/mol}.$

It is estimated that about 30% of all pollution from chemical plants comes from steam cracking, due to $CO_2$, $NO_x$, and unburned hydrocarbons unavoidably produced during steam cracking. Furthermore, as many products can be formed as a result of pyrolysis, typical yields of ethylene from ethane are approximately 50%, with even lower yields typically observed for heavier alkanes.

As an alternative to steam cracking, it has been shown that partial oxidation of these fuels may be used to produce, for example, hydrogen and olefins, with the ability to provide a high selectivity to ethylene (Bodke et al., *Science*, 285:712 (1999); Beretta et al., *J. Catal.*, 184:469 (1999)). Partial oxidation is an exothermic reaction that can be represented, for example, by the following reaction of ethane with oxygen:

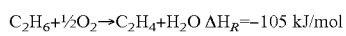

$C_2H_6 + \tfrac{1}{2}O_2 \rightarrow C_2H_4 + H_2O \; \Delta H_R = -105 \text{ kJ/mol}$ As the reaction is exothermic, the expense of providing heat to the reaction may be reduced.

It has further been shown that higher alkanes, such as decane and hexadecane, for example, may be used as fuels to provide olefins with high selectivities using partial oxidation (Krummenacher et al., *J. Catal.*, 215:332 (2003)).

SUMMARY OF THE INVENTION

A significant problem in the industry is the continued global reliance on fossil fuels, a non-renewable resource. Approximately 10% of petroleum is currently consumed in the production of olefins and related chemicals. Materials such as carbohydrates and triglycerides, on the other hand, are relatively inexpensive renewable resources that would provide a highly desirable fuel source for olefin production. For example, vegetable oils are widely produced through out the world, and their production is increasing rapidly (Demirbas, *Energy Sources*, 25:721 (2003)). Such a supply of renewable fuel could conceivably replace petroleum, for example, in the production of most small olefins.

In consideration of problems associated with the use of non-renewable fossil fuels in the production of olefins, such as pollution and expense, there is a need in the industry for a process for producing olefins from inexpensive and widely available renewable fuel sources, preferably in a partial oxidation process.

The present invention is directed to the reaction of organic compounds including at least one functional group, preferably by partial oxidation, to provide useful reaction products. It has been, unexpectedly and surprisingly, discovered that the reaction of these functionalized organic compounds, provides a reaction product wherein a significant amount of the functionality is preserved in the product. That is, the reaction under the conditions described herein of organic compound fuels that include functional groups, preferably biofeedstocks and biodiesel, provide reaction products that include functionalized organic products, preferably functionalized olefinic products.

In one aspect, the present invention provides a process for the production of an organic compound, the process including: providing a catalyst; providing a fuel source to the reactor, wherein the fuel source includes at least one organic compound that includes a functional group; and providing at least one source of oxygen to the reactor; wherein the process includes conditions effective to produce a reaction product including an olefin that includes the functional group, and wherein the olefin including the functional group is not present in the fuel source.

In a further aspect, the present invention provides a process for the production of a reaction product that includes at least one olefinic ester, the process including: providing a reactor including a catalyst; providing a fuel source including a biofeedstock that includes at least one organic compound including an ester functional group; providing at least one source of oxygen; delivering the fuel source to the reactor; delivering the source of oxygen to the reactor; mixing the fuel source and the source of oxygen to provide a fuel and oxygen mixture; and contacting the fuel and oxygen mixture with the catalyst under conditions effective to provide a reaction product including at least one olefinic ester not present in the fuel source.

In yet another aspect, the present invention provides a process for the production of a reaction product that includes at least one functionalized olefin, the process including: providing a reactor including a catalyst; providing a fuel source including a biofeedstock that includes at least one organic compound including a functional group; providing at least one source of oxygen; delivering the fuel source to the reactor; delivering the source of oxygen to the reactor; mixing the fuel source and the source of oxygen to provide a fuel and oxygen mixture; and contacting the fuel and oxygen mixture with the catalyst under conditions effective to provide a reaction product including at least one non-functionalized olefin and at least one olefin including the functional group, wherein the olefin that includes the functional group is not present in the fuel source.

DETAILED DESCRIPTION OF CERTAIN EMBODIMENTS

Figure 1:
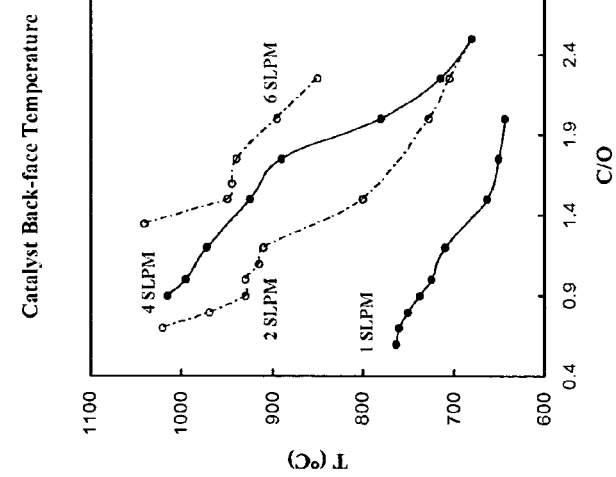
FIG. 1 is an illustrative graphical representation of reactor temperatures (catalyst backface temperature) observed during the reaction of biodiesel fuel with oxygen at flow rates of 1, 2, 4, and 6 standard liters per minute (SLPM) over a rhodium/cerium catalyst and plotted with respect to the carbon to oxygen ratios used.

The present invention provides a process and apparatus for the production of olefins, functionalized olefins and other useful materials, such as hydrogen and synthesis gas (also known as syngas, which is $H_2$ and CO), from at least one organic compound that includes a functional group. The present process may be carried out via a steam cracking process, as described above; alternatively it may, preferably, be carried out under conditions of partial oxidation.

The term "organic compound" as used herein includes, but is not limited to, a hydrocarbon compound with optional elements other than carbon and hydrogen, such as oxygen, nitrogen, sulfur, and silicon, that is classified as an aliphatic compound, cyclic compound, or combination of aliphatic and cyclic groups (e.g., alkaryl and aralkyl groups) within any one compound. The term "aliphatic compound" means a saturated or unsaturated linear or branched hydrocarbon compound. This term is used to encompass alkanes, alkenes, and alkynes, for example.

As used herein, the term "olefin" refers to an organic compound having at least one ethylenically unsaturated group.

The term "cyclic compound" means a closed ring hydrocarbon compound that is classified as an alicyclic, aromatic, or heterocyclic compound. The term "alicyclic compound" means a cyclic hydrocarbon having properties resembling those of aliphatic compounds. The term "aromatic compound" or "aryl compound" means a mono- or polynuclear aromatic hydrocarbon. The term "heterocyclic compound" means a closed ring hydrocarbon in which one or more of the atoms in the ring is an element other than carbon (e.g., nitrogen, oxygen, sulfur, etc.).

Additionally, organic compounds of the present invention may be substituted with atoms including, but not limited to, O, N, Si, or S atoms, for example, in the chain (as in an alkoxy group) as well as carbonyl groups or other conventional substitutions.

The term "biofeedstock" as used herein includes any material from living organisms including plants and animals. Typically, biofeedstock includes organic compounds that include at least one functionality or functional group including C, H, and O, and further may include small amounts of S, N, and P.

Biofeedstocks can be used as a fuel source in the present invention and include, but are not limited to, carbohydrates, triglycerides, polyols, and biodiesel.

The term "biodiesel" as used herein includes mono-alkyl esters of long chain fatty acids derived from vegetable oils or animal fats by reaction with an alcohol in the presence of a catalyst. Biodiesel includes, for example, methyl esters formed by reaction of triglycerides with methanol or ethanol, yielding the mono-alkyl esters and glycerin. For instance, biodiesel produced from soy oil typically provides five major ester compounds, with the typical composition of those compounds approximately as follows: methyl palmitate (12%), methyl stearate (5%), methyl oleate (25%), methyl linoleate (52%), and methyl linolenate (5%), with double bonds, all in the cis configuration, occurring after carbons 9, 12, and 15 (counting the carbonyl carbon as "carbon 1") for fatty acids including 1, 2, and 3 double bonds, respectively. Biodiesel that meets the requirements as set forth in the standards of ASTM D 6751 is useful as a domestic, renewable fuel for diesel engines.

Furthermore, biodiesel useful in this invention may also be present in the form of a blend of pure biodiesel and a petroleum-based diesel fuel. Thus, biodiesel as used herein may include both pure biodiesel and blends with petroleum diesel.

The term "functionalized" or "functionalized group" as used herein means an atom or group of atoms, acting as a unit, that replaces a hydrogen atom in a hydrocarbon molecule, and whose presence imparts characteristic properties to the molecule. Functional groups of the present invention include, but are not limited to, alcohols, aldehydes, carboxylic acids, carboxylic acid esters, ketones, acid halides, amides, ethers, and alkyl halides. Furthermore, more than one functional group, of the same type or of different types, may be present on any single organic compound.

The term "carbohydrate" as used herein includes compounds produced by photosynthetic plants and include carbon, hydrogen, and oxygen, typically in the ratio 1:2:1. Carbohydrates include sugars, starches, celluloses, and gums.

The terms "vegetable oil" and "animal oil" refer to oils and/or fats from vegetable or animal sources, respectively. Such oils include, for example, refined and/or unrefined oils, purified and/or unpurified oils, and used oils. "Used oils" refer to vegetable and/or animal oils that have been used in the processing of another material. A used vegetable or animal oil is typically a by-product of a separate process, such as the frying of foods. The substances "yellow grease" and "brown grease" are terms known in the art to describe two types of used oils that are differentiated by their degree of contamination (such as the amount of free fatty acids remaining in the oil after frying foods), with brown grease including a greater amount of contaminants.

The term "higher alcohol" as used herein means an organic compound including at least one alcohol functional group and having a carbon chain length of at least 3 carbons.

Significantly, the process of the present invention is directed to a process and apparatus for production of relatively high selectivities of olefins and functionalized olefins from fuel sources that may include organic compounds which include at least one functional group, and preferably from biofeedstock fuels. Product selectivities as used herein are reported on a carbon atom and hydrogen atom basis. For example, hydrogen and water selectivities are reported on a hydrogen atom basis and the remaining reaction products, such as olefins, olefinic esters, CO, and $CO_2$ are typically reported on a carbon atom basis. Selectivities, for example carbon atom selectivities, are calculated as the ratio of the moles of a specific product to the total moles of all the products, scaled by, in the case of carbon atom selectivity, the number of carbon atoms in the species. Similarly, hydrogen atom selectivities are calculated as the ratio of moles of a specific product to the total moles of all the products, scaled by the number of hydrogen atoms in the species. All selectivities calculated for the reactions herein sum to 100%. The carbon atom selectivity percentage, Sj, to the general product species $C_{xj}H_{yj}O_{zj}$ for total product i is:

$$S_j = (x_j F_j / \Sigma x_i F_i) \times 100$$

where Fj is the molar flow rate of species j per minute that contains xj carbon atoms, and Fi is the flow rate of any carbon-containing species $C_{xj}H_{yj}O_{zj}$.

Functionalized organic fuels may be present in gaseous, liquid, or solid form prior to contact with the catalyst. In the present processes, the fuel source, if not provided in gaseous form, is preferably vaporized then mixed, preferably substantially simultaneously vaporized and mixed, with a source of oxygen, and the fuel and oxygen mixture is contacted with a catalyst. A further reactive and/or nonreactive gas may also be present.

The catalyst is preheated to a specified temperature, after which either energy is fed to the catalyst to maintain the temperature, or the reaction is maintained under autothermal conditions. The fuel and oxygen mixture is also heated prior to the reaction, and, depending on reaction conditions, a certain "steady-state catalyst backface temperature" is reached.

The fuel and oxygen are fed to the catalyst at specified flow rates and catalyst contact times that, together with the reaction temperatures, provide the reaction products. Advantageous products obtainable with the present process include $H_2$, CO, $CO_2$, $H_2O$, ethylene, propylene, 1-butene, 1-pentene, and other $\alpha$-olefins.

Surprisingly, it was found that some of the functional groups of the organic fuel sources of the invention survive the reaction product to provide, for example, functionalized olefins. Without being held to any particular theory, it is believed that when the fuel and oxygen are combined and contact the catalyst under reaction conditions described herein, a portion of the reactant molecules react with the oxygen and dissociate to form oxidation products, such as $H_2$, CO, $CO_2$, and $H_2O$, as well as heat. It is further believed that under the present conditions, only the amount of heat required to break carbon-carbon single bonds in the balance of the reactant molecules is provided. Thus, functionality originally present on reaction molecules, as well a carbon-carbon double bonds, are preserved in the remaining reactant molecules. Product compounds may be determined by calculating their selectivities, and the presence of the functionalities may be determined by GC/GC-MS analysis. Under the processes and reaction conditions described herein, it is believed that at least about 20 mole percent of the functional groups present in the reactant are present in the product after reaction, preferably at least about 50 mole percent, and more preferably at least about 75 mole percent.

Fuels, Reaction Products, and C/O Ratios

Fuels useful in the present invention include organic compounds that include at least one functional group, and preferably may include two or more functional groups. Exemplary functional groups include, but are not limited to alcohols, aldehydes, carboxylic acids, carboxylic acid esters, ketones, acid halides, amides, ethers, alkyl halides, and combinations thereof. Surprisingly, it has been found that the functionality of the organic compounds that may be used as a fuel source is to some extent conserved after reaction of the fuel, as described herein. Without being held to any particular theory, it is believed that the oxidation of a certain amount of the fuel provides products that include $H_2$, CO (i.e., syngas), $CO_2$, water, and heat. Heat is provided in such an amount that certain carbon-carbon bonds of the remaining functionalized organic molecules of the fuel not oxidized are broken such that the reaction products further include, in addition to the oxidation products, at least one organic compound that includes a functional group and at least one organic compound that does not include a functional group. Preferably, at least one of these organic compounds is an olefinic organic compound. Thus, reaction products of the present invention advantageously include olefins, functionalized olefins, dienes, functionalized dienes, polyenes, functionalized polyenes, and combinations thereof. Preferred non-functionalized olefinic reaction products of the present invention include ethylene and propylene.

Fuels of the present invention advantageously include biofeedstocks, which typically include, for example, at least one compound selected from carbohydrates, triglycerides, polyols, and any combination thereof. Triglycerides include, for example, animal fats, and vegetable and animal oils. Vegetable oils and animal oils, as used herein refer to both used and nonused oils, and combinations thereof, wherein used vegetable and animal oils are those that have been employed for another purpose, such as frying food, thus may, for example, be partially consumed, contain contaminants, etc. Such materials are known in the art, for example, as yellow grease and brown grease. These compounds, particularly the vegetable oils, are widely available and relatively inexpensive renewable resources. Vegetable oils useful in the processes of the present invention include, but are not limited to, soy oil, palm oil, olive oil, sunflower seed oil, safflower seed oil, rape seed oil, wheat germ oil, corn oil, peanut oil, canola oil, grapeseed oil, castor oil, coconut oil, and any combination thereof.

Additionally, biofeedstocks useful as fuels in the present invention further include compounds including at least one methyl carboxylic acid ester functional group, compounds including at least one ethyl carboxylic acid ester functional group, compounds including at least one higher alcohol carboxylic acid ester functional group, biodiesels, and any combination thereof.

The carbon to oxygen (C/O) atomic ratio of the fuel and oxygen source mixture reacted is believed to be significant in determining the reaction products. For example, selectivities of olefins, including functionalized olefins and olefinic esters, are typically produced using C/O atomic ratios preferably at least about 0.8, and more preferably at least about 1.5. Also, preferred C/O atomic ratios for the production of olefins are preferably no greater than about 5, and more preferably no greater than about 3. Furthermore, a decrease in the C/O ratio, with the flow rate held constant, typically will cause a decrease in olefin production and an increase in production of the combustion products ($CO_2$ and $H_2O$). Additionally, in combination with the selected flow rate, the C/O atomic ratio of the reactants influences the reaction temperature.

At these C/O atomic ratios ethylene, propylene, and α-olefins are preferably produced at a selectivity of at least about 7%, 1%, and 3%, respectively, and more preferably ethylene, propylene, and α-olefins are produced at a selectivity of about 25%, 9%, and 25%, respectively.

To produce syngas, for example, a preferred C/O atomic ratio is at least about 0.3, a more preferred atomic ratio is at least about 0.5, and even more preferably the atomic ratio is at least about 0.6 C/O. To produce syngas by the processes of the present invention, C/O atomic ratios are preferably no greater than about 2, and more preferably no greater than about 1.

Using these preferred C/O ratios, and under the preferred processes of the present invention, the selectivity of syngas is preferably at least about 60 percent. That is, of the total reaction products, at least about 60 percent of the product is syngas. More preferably syngas is produced at a selectivity of at least about 85 percent. Additionally, the selectivity of syngas under these preferred process conditions is preferably no greater than about 100 percent, and more preferably no greater than about 90 percent.

Oxygen Sources

The fuel source of the present invention is mixed with an oxygen source prior to contacting a catalyst. The oxygen source may be introduced to the reactor in liquid form or in gaseous form; however a gaseous form is preferred. The fuel source and oxygen source are preferably vaporized and mixed, preferably substantially simultaneously vaporized and mixed, prior to contacting the catalyst. Preferred oxygen sources include air, oxygen-enriched air, molecular oxygen, oxygen-enriched gases (e.g., oxygen-enriched nitrogen, argon, helium, xenon, radon, and/or krypton), and combinations thereof. The choice of oxygen source may be selected as appropriate to the application. For instance, for applications such as automotive fuel reforming, air is typically preferred. Also, for large scale operations, air is generally an efficient and economical oxygen source. However, for such applications as olefin production, pure $O_2$ may be preferred. That is, certain preferred processes of the present invention include a source of oxygen that is substantially free of nitrogen. The processes of the present invention are appropriate for a wide variety of oxygen sources. Preferably, substantially all of the oxygen introduced into the reaction is consumed in a partial oxidation step.

For preferred processes including air as the oxygen source, nitrogen is typically present in the air in an atomic ratio of no greater than about 6:1 nitrogen to oxygen. More preferably, nitrogen is present in the air in an atomic ratio of no greater than about 4:1 nitrogen to oxygen. For reactions producing syngas, if air is used as the oxygen source, nitrogen is most preferably present in the air in an atomic ratio of at least about 3.5:1 nitrogen to oxygen. Also, most preferably, if air is used as the oxygen source for syngas production, nitrogen is present in an atomic ratio of no greater than about 4:1 nitrogen to oxygen.

Other Feed Gases/Inert Carrier Gases

The fuel and oxygen mixture may, optionally, be mixed with an additional carrier gas. This additional gas may be reactive, such as $H_2O$, or it may be an inert gas. Any inert gas may be used, such as nitrogen, argon, and helium.

Additionally, processes of the present invention may advantageously be reacted without adding water to the reaction. This is advantageous because there is no need for the added step of removing unreacted water from the products. Furthermore, by not adding water to the reactions, the reactions typically yield a higher selectivity of desired products and greater product output. Therefore, water is preferably not present. The present processes, however, are also suitable for reaction in the presence of water, preferably added in the form of water vapor. For reactions in which water is present, water is preferably present in a ratio of no greater than about 20, water molecule to carbon atom. More preferably, if water is present, the water is present in a ratio of no greater than about 10, water molecule to carbon atom.

Catalysts

A preferred catalyst of the present invention includes rhodium. Additionally, other metals and/or oxides thereof can be advantageously used in combination with rhodium. Herein, the term "metals" is understood to include metals and metalloids. These metals include those selected from Groups 2, 3, 4, 5, 6, 7, 8, 9, 10, 11, 12, 13, and 14 of the Periodic Table, using the IUPAC format which numbers the groups in the Periodic Table from 1 to 18. Preferably, the catalyst includes rhodium and/or oxide thereof, and at least one other metal and/or oxide thereof selected from the group of Ce, Pd, Pt, Ru, Ir, Os, Mg, Cu, Si, Ti, V, Zn, La, Sm, Zr, Hf, Cr, Mn, Fe, Co, Ni, Cu, Y, Sn, Sb, Re, Eu, Yb, and combinations of these metals and/or oxides thereof. More preferably, the catalyst includes rhodium and/or oxide thereof, and at least one other metal and/or oxide thereof selected from the group of Ce, Pt, Pd, Ru, Ir, Al, Zr, and combinations of these metals and/or oxides thereof. Even more preferably, the catalyst includes rhodium and/or oxide thereof, and at least one metal and/or oxide thereof selected from the group of Ce, Al, Zr, and combinations of these metals and/or oxides thereof. Yet more preferably, the at least one metal and/or oxide thereof is cerium.

Preferably, rhodium is included in the catalyst in an amount of at least about 10% of the total weight of the metal catalyst. Other metals, if present, are present in a total amount of preferably no greater than about 90%, based on total weight of the metal catalyst. A preferred embodiment of the invention includes a catalyst including a mixture of rhodium and cerium in a 50/50 weight ratio, based on total weight of the metal catalyst. Other preferred embodiments include catalysts including a mixture of rhodium and cerium in ratios of 70%/30% and 80%/20% rhodium to cerium, based on total weight of the metal catalyst.

The source of the metal can be metal salts, such as, for example, nitrates, phosphates, sulfates, chlorides, and bromides. A preferred salt for use with rhodium is rhodium nitrate. If the desired catalyst is a mixture of metals, it is preferable that the salts are compatible. "Compatible salts" are, for instance, salts having the same anion or cation and/or salts that dissolve in the same solvent. Provision of compatible salts may advantageously be accomplished by using the same type of organometallic compound. For example, for a catalyst of rhodium and cerium, rhodium nitrate and cerium nitrate may preferably be used. If, for example, a catalyst of platinum and ruthenium is desired, a mixture of chloroplatanic acid and hexachlororuthenate may advantageously be used.

Alternatively, the metal source can be any method that will deposit or coat a metal on a catalyst support, such as, but not limited to, sputtering, evaporation, CVD deposition, for example.

Depending upon the type of reactor used, the catalyst may include a support or it may be unsupported. For catalysts including a support, preferred supports of the present invention include a monolithic carrier, that is, a carrier of the type including one or more monolithic bodies having a plurality of finely divided gas flow passages extended therethrough. Such monolithic carrier members are often referred to as "honeycomb" type carriers and are well known in the art. A preferred form of such carrier is made of a refractory, substantially inert, rigid material that is capable of maintaining its shape and a sufficient degree of mechanical strength at temperatures of, for example, about 1500° C. Typically a material is selected for the support that exhibits a low thermal coefficient of expansion, good thermal shock resistance, and low thermal conductivity. Typical supports include, but are not limited to, metal monolith, metal foam, ceramic monolith, foam ceramic monolith, solid spheres, porous spheres, pellets, gauze, wires, plates, and combinations thereof.

A more preferred support of the present invention includes a ceramic foam monolith such as disclosed in U.S. Pat. No. 4,568,595 (Morris), which discloses honeycombed ceramic foams with a surface having a ceramic sintered coating closing off the cells, and U.S. Pat. No. 4,253,302 (Asano et al.), which discloses a foamed ceramic containing platinum/rhodium catalyst as an exhaust gas catalyst. The foam structure is characterized by the number of pores per linear inch (ppi). Preferred ceramic foam monoliths include those with at least about 10 ppi (approximately 394 pores per meter). Preferably monoliths of the present invention include those with no greater than about 100 ppi (approximately 3937 pores per meter). A more preferred ceramic foam monolith includes about 80 ppi (approximately 3110 pores per meter).

Preferred supports further include supports made from metals and metal oxides selected from the group of γ-alumina and magnesium aluminum silicate (cordierite). Preferably, the monolith support is washcoated to increase the surface area of the catalyst and to reduce the pore size of the monolith, thereby not only increasing the surface area, but also decreasing the probability that a species will pass through the catalyst without reacting on the surface. The washcoat is typically applied by coating an aqueous solution of, for example γ-alumina on the monolith and allowing the aqueous solvent to evaporate off.

Reactors

The present invention may be carried out using any reactor apparatus which will provide a vaporized feed gas of the invention at the selected temperature and at the selected flow rate to a selected catalyst heated to a selected temperature, as described herein. Such reactor types include, but are not limited to, autothermal reactors, fluidized bed reactors, packed bed reactors, catalytic wall reactors, riser reactors, and any combination thereof. A particularly preferred reactor is one in which partial oxidation may be carried out under autothermal conditions, that is, once the catalyst has reached a pre-heat temperature, no further heat input is required and the process is driven forward by the energy released from the exothermic partial oxidation reaction.

A preferred reactor material is quartz; however any material, such as ceramic, is appropriate for use in a reactor, provided it can withstand the reaction temperatures. The reactor can be of any shape, provided contact time with the catalyst is maintained. A tube shaped reactor is preferred. Additionally, a tube shaped reactor can be of any length desired, provided catalyst contact time is maintained. Preferred tube shaped reactors are preferably at least about 45 centimeters (cm) in length, and more preferably at least about 55 cm in length. Preferred reactors are typically no longer than about 80 cm in length. Additionally, the tube reactor can be of any convenient inner diameter, provided catalyst contact time is maintained and the reactor is able to adequately hold the catalyst. Preferred reactors of the present invention have an inner diameter of, typically, at least about 18 millimeters (mm). Typically, the preferred reactors of the present invention have inner diameters of no greater than about 5 cm.

Reaction Temperatures

The fuels, in particular fuels that are liquid or solid at room temperature, prior to contact with the catalyst, are typically pre-heated to form a vapor that is mixed with the oxygen source. Preferred preheat temperatures of the fuels of the present invention, which are vaporized and contacted with the oxygen source substantially simultaneously, are typically at least about 25 degrees Celsius (° C.), more preferably at least about 50° C., above the boiling point of the fuel source prior to contacting the catalyst. Furthermore, fuel preheat temperatures are typically no greater than about 150° C., more preferably no greater than about 100° C., above the boiling point of the fuel source prior to contacting the catalyst.

Additionally, the catalyst is preheated to a temperature of, preferably about 280° C. prior to introducing the fuel and oxygen mixture to the reactor. In an autothermal process, once the catalyst is "ignited," that is, it reaches the pre-heat temperature, no further heat needs to be supplied to the system. For non-autothermal processes, however, energy must be supplied to the system to maintain the ignition temperature of the catalyst.

Typically, the preferred reactor temperatures of any acceptable reactor apparatus (that is, the temperature of the backface of the catalyst after contact with the feed gas) at which partial oxidation of fuel occurs is at least about 600° C., more preferably at least about 750° C., and most preferably, at least about 850° C. Preferably, reactor temperatures are no greater than about 1,400° C., and more preferably, no greater than about 1,100° C.

Catalyst Contact Times

Preferred flow rates for the fuel and oxygen feed to the catalyst are a factor in providing preferred time periods during which the vaporized fuel and oxygen mixture contacts the catalyst. A preferred contact time of the vaporized fuel and oxygen mixture with the catalyst is at least about 5 milliseconds (ms), and more preferably at least about 10 ms. Additionally, the vaporized fuel and oxygen mixture preferably contacts the catalyst for a period of no greater than about 50 ms, and more preferably no greater than about 25 ms.

Flow Rates

Preferred flow rates are a factor in providing preferred time periods during which the vaporized fuel and oxygen mixture contacts the catalyst. To provide the preferred contact times for the production of the desired reaction products, the mixture of the fuel source and the source of oxygen preferably contacts the catalyst at a flow rate of at least about $1.5 \times 10^5$ $hr^{-1}$ Gas Hourly Space Velocity (GHSV). Additionally, the fuel source and oxygen mixture preferably contacts the catalyst at a flow rate of no greater than about $6 \times 10^6$ $hr^{-1}$ GHSV.

More preferably, and particularly for the production of syngas, the flow rate of the fuel and oxygen source is at least about $6 \times 10^5$ $hr^{-1}$ GHSV, and most preferably at least about $1.2 \times 10^6$ $hr^{-1}$ GHSV.

More preferably, for the production of smaller olefins, such as ethylene and propylene, the flow rate of the fuel and oxygen source is at least about $1.2 \times 10^6$ $hr^{-1}$ GHSV, and most preferably at least about $1.8 \times 10^6$ $hr^{-1}$ GHSV.

EXAMPLES

In the following examples an automotive gasoline fuel injector (Delphi Automotive Company, Troy, Mich.) was attached to the top of a quartz reactor tube and used as the fuel delivery method to facilitate vaporization and mixing of reactants before contacting the catalyst. Pressurized fuel at 5 pounds per squared inch as read from a pressure gauge (psig) was fed into the injector, which was computer operated at a frequency of about 10 Hertz (Hz), with the percentage of time that the injector remains open (i.e., duty cycles) of about 1% to about 15%. Thus, the liquid flow rate delivered by the injector was controlled accurately by the pressure in the fuel supply tank and by the duty cycle. The fuel delivery rate was calibrated at different pressures, frequencies, and duty cycles prior to conducting the following examples and was found accurate to within ±2%.

Reactor

Figure 19:
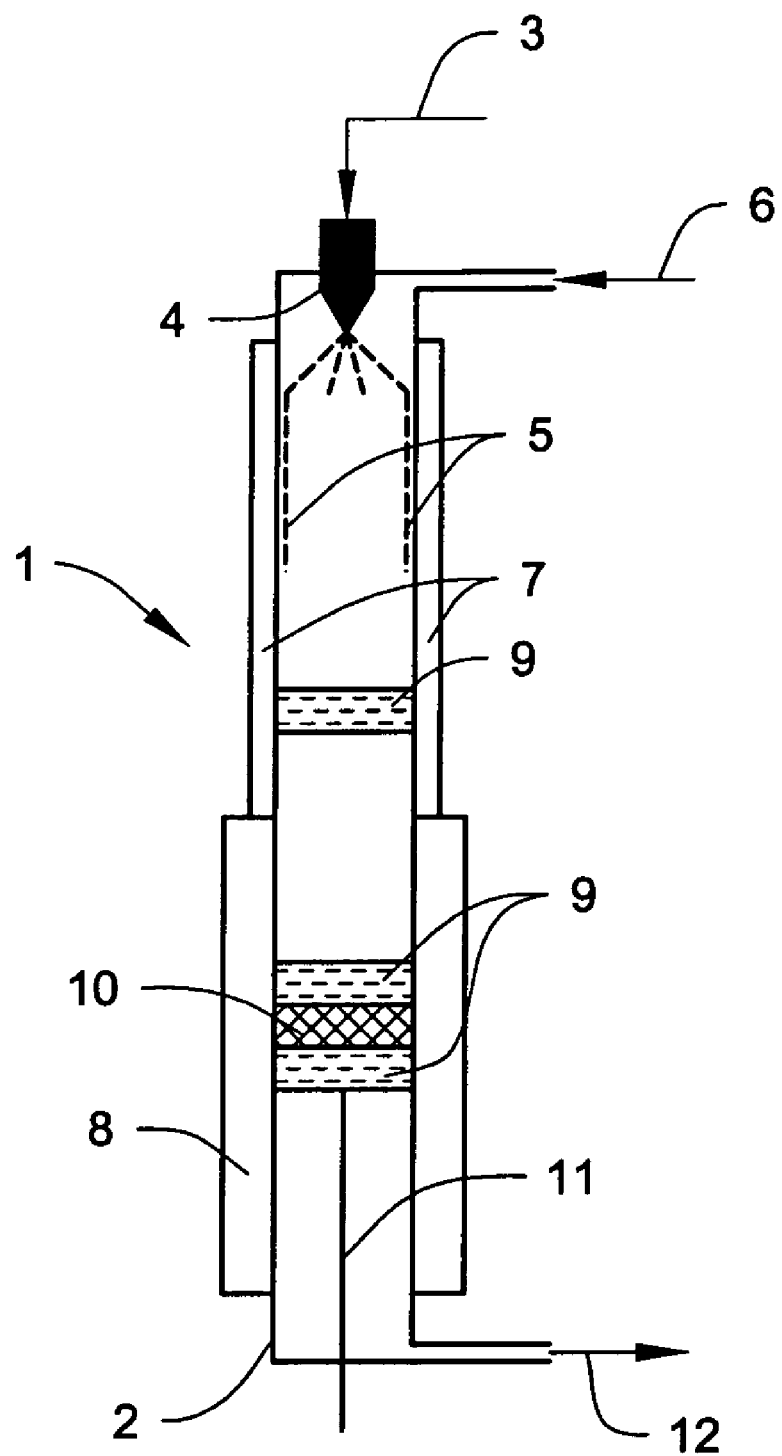
FIG. 19 is a schematic diagram of an exemplary autothermal reactor.

The reactor apparatus used in the following examples is shown in FIG. 19. The reactor (1) consisted of a quartz tube (2) with a 19 mm inner diameter and was 55 centimeters (cm) in length. The fuel (3) was delivered to the reactor from the top, using a fuel injector (4) as described above, creating a film of fuel on the reactor walls (5). The oxygen source (6) used, air, was separately delivered to the reactor from the top. The reactor walls were pre-heated to a temperature of about 250° C. to 400° C., depending on the boiling point of the fuel. The pre-heat temperature was at least about 50° C. and no greater than about 150° C. higher than the boiling point of the fuel used. Heating tape (7) and insulation (8) was provided around the reactor to prevent dissipation of heat. Blank monoliths (9) were provided on either side of the catalyst (10) to act as a heat shield. The back face temperature of the catalyst was measured with a thermocouple (11) and the reaction products (12) were recovered at the downstream side of the catalyst.

Oxygen Source

Air, rather than pure $O_2$, was used in the following examples to reduce the possibility of flames and explosions.

Catalyst Preparation

Alfa Asear #1263 rhodium nitrate solution (0.947 grams, available from Alfa Asear, Ward Hill, Mass.) and 0.370 g cerium nitrate (Alfa Aesar #11329, Alfa Asear, Ward Hill, Mass.) were mixed with 20 milliliters (ml) of deionized water and placed in a petri dish. Then, an 80 pores per inch (PPI) alumina monolith, available from ZUES Corporation (Kokomo, Ind.) weighing 2.163 grams (g) was placed in the petri dish with the metal salt mixture, and the mixture was allowed to adsorb onto the monolith by capillary forces in the high surface area monolith. The water was then allowed to evaporate from the mixture for approximately 1 week. Once the water evaporated, the monolith was heated in an oven to about 600° C. in air for about four hours.

Biodiesel Fuel

Biodiesel derived from soy oil was used as the fuel in the following examples. The biodiesel used was a high purity (B100) fuel grade, purchased from West Central Soy (Ralston, Iowa).

Product Analysis

The product stream typically included at least one, and preferably a mixture of two or more, of the following gases: hydrogen, nitrogen, oxygen, carbon monoxide, and carbon dioxide (referred to herein as permanent gases), as well as including, after cooling, reactant products including carbon compounds, preferably olefinic compounds, and typically some un-reacted fuel. Analyzing this product stream using a gas chromatograph or mass spectrometer can be challenging because columns that can separate liquids typically cannot separate permanent gases. Therefore, a dual column system, including a pre-column, was adapted for use in the present examples (Allen K. Vickers; Daron Decker; Jason Ellis, "PLOT column configurations for the gas chromatic analysis of ozone precursors" J&W Scientific publication, August, 1998) and installed in a 5890 Series II Hewlett-Packard Gas Chromatograph (GC) (Hewlett Packard, Palo Alto, Calif.). Helium was used as the carrier gas. The product samples were injected into a DB-1 capillary pre-column (15 meters (m) in length, 0.32 mm Inner Diameter (ID), 0.25 μm dimethylsiloxane (DMSO) film at the injection port. The permanent gases typically traveled faster through the pre-column than did the hydrocarbons. The 4-way switching valve was initially set at position 1, where the permanent gases were sent to a Heyesep D (Alltech, model 100/120, Deerfield, Ill.) packed column (9 m in length, 2.2 mm ID). This column separated the permanent gases at room temperature. After the permanent gases left the pre-column, the valve was switched to position 2, sending the hydrocarbons to a DB-1 (J&W Scientific, model DB-1, Folsom, Calif.) capillary column (60 m in length, 0.32 mm ID, 0.25 μm DMSO film). The permanent gases were analyzed using a TCD (thermal conductivity detector) and the hydrocarbons were analyzed using an FID (flame ionization detector) which were both supplied with the Gas Chromatograph (Hewlett-Packard, Palo Alto, Calif.). Nitrogen was used as the calibration standard, carbon and hydrogen balances typically closed within ±8% error. All products were incinerated in a fume hood and vented.

This GC system was insufficient to analyze the larger hydrocarbon products that resulted from the partial oxidation of biodiesel because the large number of GC peaks made the analysis intractable. Therefore, a GC mass spectrometer (GC-MS) (Hewlett-Packard, Palo Alto, Calif.) was used to analyze heavier products in a separate analysis. The hydrocarbon products were condensed in isopropanol and analyzed. In all cases the results showed that most of the hydrocarbon products were olefins and olefinic esters. The GC-MS also quantified alkanes and olefin fractions.

In the following examples, the flow rate was calculated using standard liters per minute (SLPM), which is related to Gas Hourly Space Velocity (GHSV). GHSV is defined as the volume of gas feed per hour per volume of catalyst, the volume of catalyst calculated from the weight percent and standard densities of the catalyst. The relation of GHSV to SLPM is:

GHSV=SLPM*60/volume of the catalyst

For the catalysts used in the following examples, SLPM may be converted to GHSV using the relation: 1 SLPM=3× $10^5$ $hr^{-1}$.

Example 1

A catalyst of about 2.5 weight percent rhodium and about 2.5 weight percent cerium, based on total weight of catalyst and support, on an alumina monolith was prepared according to the method described above.

A reactor apparatus was assembled as described above and the rhodium/cerium catalyst was placed in the reactor. The reactor was maintained at a pressure of approximately 1 atmosphere (atm) throughout the process. Two blank 80 ppi ceramic foam monoliths (Vesuvius Hi-Tech Ceramics, Alfred Station, N.Y.) were placed immediately upstream (the region of the reactor between where the fuel and oxygen enter the reactor and the catalyst) and downstream from the catalyst. The blank monoliths acted as axial heat shields and were used to promote additional radial mixing. All three monoliths were wrapped with FIBERFRAX (Unifrax Corporation, PS3338, Niagara Falls, N.Y.) alumina-silica paper to avoid bypassing of gasses between the monoliths and the reactor wall. A chromel-alumel k-type thermocouple (Omega Engineering, Inc., Stamford, Conn.) was placed between the backside of the upstream blank monolith and the catalyst to measure the "back face" temperature. Alumina-silica insulation (Unifrax Corporation, Niagara Falls, N.Y.) was placed around the reactor to reduce radial heat loss.

Oxygen and nitrogen (the oxygen source) at the atomic ratio of approximately 3.76 N/O were initially heated to about 350° C. and admitted to the reactor to heat the catalyst and walls of the reactor. The flow rates of the oxygen source, high purity $N_2$ and $O_2$, entering the reactor from high-pressure cylinders were adjusted to approximately 4 standard liters per minute (SLPM) using mass flow controllers that were accurate to ±0.05 SLPM. The oxygen source released heat to the catalyst, heating it to a temperature of about 280° C., measured at the back face of the catalyst using a thermocouple. The catalyst ignited within about 15 seconds.

Liquid biodiesel (B100, West Central Soy, Ralston, Iowa) was then introduced at a flow rate of 68 grams/hr through the fuel injector into the pre-heated section of the reactor. The fuel vaporized and mixed with the oxygen source at a temperature of about 350° C. and at a C/O ratio of about 0.9 (atomic ratio of 0.9:1 carbon to oxygen). The fuel and oxygen mixture contacted the catalyst at a contact time of approximately 12 milliseconds (ms). The reaction was allowed to run for about 30 minutes, at which time the backface temperature of the catalyst stabilized at approximately 1015° C., heated as a result of the exothermicity of the reaction.

A sample of the reaction product was then removed from the reactor using a 500 microliter (μl) syringe and analyzed as described above. The oxygen source was shut off, then the fuel source was shut off. The oxygen source was then allowed to flow again for approximately one minute to burn off any potential amount of coke that may have formed on the catalyst surface during the reaction. The oxygen source was then shut off.

In reporting the selectivities of the reaction products obtained, the percentage for total hydrocarbons includes the shorter chain hydrocarbons, such as ethylene, propylene, 1-butene, and 1-pentene, as well as longer chain hydrocarbons (i.e., "higher hydrocarbons") that include olefins, functionalized olefins, and olefinic esters. For instance, in the present example, selectivity of the hydrocarbon reaction products is reported as 8%, with 7% being ethylene, 1% being propylene, and 0% 1-butene, 1-pentene, or higher hydrocarbons. Thus, carbon selectivity of the reported products is 97% (81% CO, 8% $CO_2$, and 8% hydrocarbons). The remaining 3% include various minor products, such as alkanes, which are not reported in the results.

The reaction products obtained in Example 1 were $H_2$ (88%), CO (81%), $H_2O$ (3%), $CO_2$ (8%), ethylene (7%), propylene (1%), 1-butene (0%), and 1-pentene (0%): total hydrocarbons (8%) the values representing hydrogen atom or carbon atom selectivity.

Example 2

The process of example 1 was followed, except that the flow rate of the oxygen source and the fuel source was 1 SLPM, the catalyst contact time was 48 ms, and the catalyst back face temperature was about 737° C. The reaction products obtained were $H_2$ (13%), CO (32%), $H_2O$ (35%), $CO_2$ (21%), ethylene (9%), propylene (4%), 1-butene (3%), and 1-pentene (0%): total hydrocarbons (44%).

Example 3

The process of example 1 was followed, except that the flow rate of the oxygen source and the fuel source was 2 SLPM, the catalyst contact time was 24 ms, and the catalyst back face temperature was about 930° C. The reaction products obtained were $H_2$ (61%), CO (64%), $H_2O$ (12%), $CO_2$ (12%), ethylene (14%), propylene (3%), 1-butene (1%), and 1-pentene (0%): total hydrocarbons (18%).

Example 4

The process of example 1 was followed, except that the atomic carbon to oxygen ratio used was about 1.5 C/O. The catalyst back face temperature for this reaction was about 925° C. The reaction products obtained were $H_2$ (11%), CO (24%), $H_2O$ (11%), $CO_2$ (11%), ethylene (25%), propylene (7%), 1-butene (4%), and 1-pentene (0%): total hydrocarbons (56%).

Example 5

The process of example 4 was followed, except that the flow rate of the oxygen source and the fuel source was 1 SLPM, the catalyst contact time was 48 ms, and the catalyst back face temperature was about 663° C. The reaction products obtained were $H_2$ (1%), CO (10%), $H_2O$ (27%), $CO_2$ (14%), ethylene (4%), propylene (4%), 1-butene (2%), and 1-pentene (1%): total hydrocarbons (74%).

Example 6

The process of example 4 was followed, except that the flow rate of the oxygen source and the fuel source was 2 SLPM, the catalyst contact time was 24 ms, and the catalyst back face temperature was about 800° C. The reaction products obtained were $H_2$ (2%), CO (15%), $H_2O$ (17%), $CO_2$ (11%), ethylene (17%), propylene (6%), 1-butene (5%), and 1-pentene (1%): total hydrocarbons (67%).

Example 7

The process of example 4 was followed, except that the flow rate of the oxygen source and the fuel source was 6 SLPM, the catalyst contact time was 8 ms, and the catalyst back face temperature was about 950° C. The reaction products obtained were $H_2$ (11%), CO (22%), $H_2O$ (11%), $CO_2$ (12%), ethylene (23%), propylene (5%), 1-butene (2%), and 1-pentene (0%): total hydrocarbons (58%).

Carbon to Oxygen Ratios

Further examples were carried out using C/O ratios in the combined feed gas and oxygen source from the lowest C/O being about 0.6 to the highest C/O ratio being about 2.5 without any evident deterioration in performance over at least 50 hours. Results of catalyst backface temperatures, conversion of biodiesel and oxygen over the rhodium/cerium catalyst, product selectivities, and distribution of olefins from biodiesel are shown in FIGS. 1 to 12.

A graph of reactor temperatures (catalyst backface temperature) observed during the reaction of biodiesel fuel with oxygen at flow rates of 1, 2, 4, and 6 standard liters per minute (SLPM) over a rhodium/cerium catalyst and plotted with respect to the carbon to oxygen ratios used is provided in FIG. 1.

Figure 2:
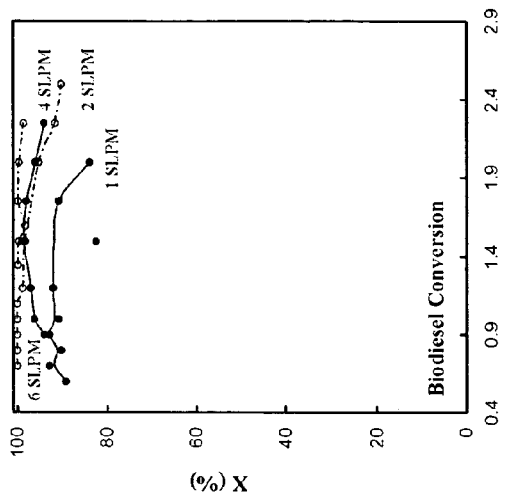
FIG. 2 is an illustrative graphical representation of the conversion percentages of the biodiesel fuel observed in the reaction of biodiesel fuel with oxygen at flow rates of 1, 2, 4, and 6 SLPM over a rhodium/cerium catalyst and plotted with respect to the carbon to oxygen ratios used.
Figure 3:
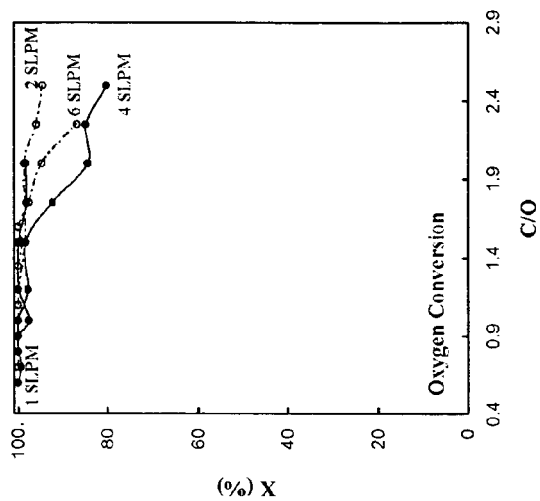
FIG. 3 is an illustrative graphical representation of the conversion percentages of the oxygen provided observed in the reaction of biodiesel fuel with oxygen at flow rates of 1, 2, 4, and 6 SLPM over a rhodium/cerium catalyst and plotted with respect to the carbon to oxygen ratios used.
Figure 4:
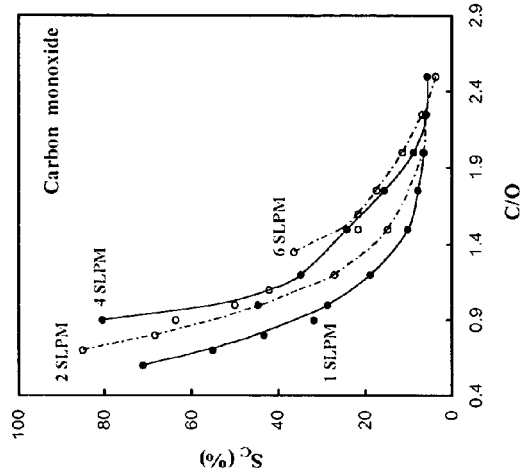
FIG. 4 is an illustrative graphical representation of the product selectivity of hydrogen obtained from reaction of biodiesel fuel with oxygen at flow rates of 1, 2, 4, and 6 SLPM over a rhodium/cerium catalyst and plotted with respect to the carbon to oxygen ratios used.
Figure 6:
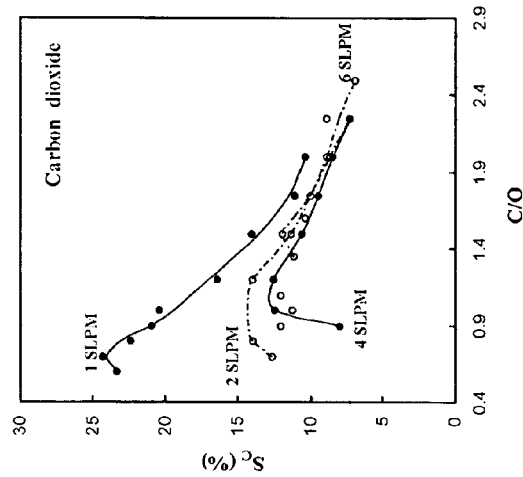
FIG. 6 is an illustrative graphical representation of the product selectivity of carbon monoxide obtained from reaction of biodiesel fuel with oxygen at flow rates of 1, 2, 4, and 6 SLPM over a rhodium/cerium catalyst and plotted with respect to the carbon to oxygen ratios used.
Figure 5:
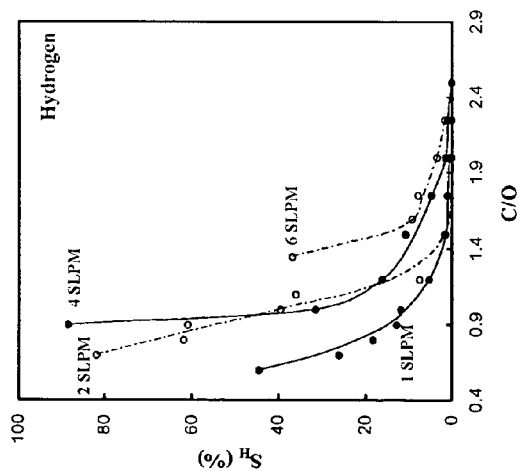
FIG. 5 is an illustrative graphical representation of the product selectivity of water obtained from reaction of biodiesel fuel with oxygen at flow rates of 1, 2, 4, and 6 SLPM over a rhodium/cerium catalyst and plotted with respect to the carbon to oxygen ratios used.
Figure 7:
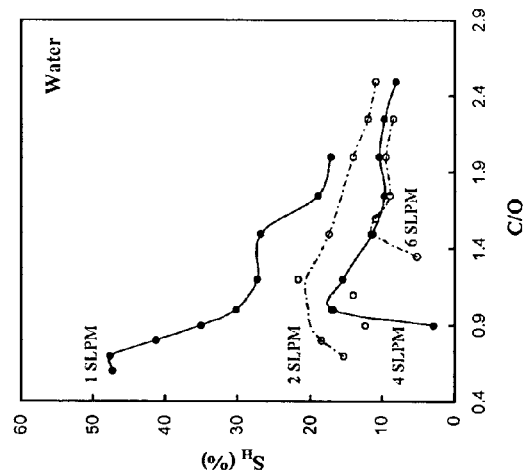
FIG. 7 is an illustrative graphical representation of the product selectivity of carbon dioxide obtained from reaction of biodiesel fuel with oxygen at flow rates of 1, 2, 4, and 6 SLPM over a rhodium/cerium catalyst and plotted with respect to the carbon to oxygen ratios used.
Figure 10:
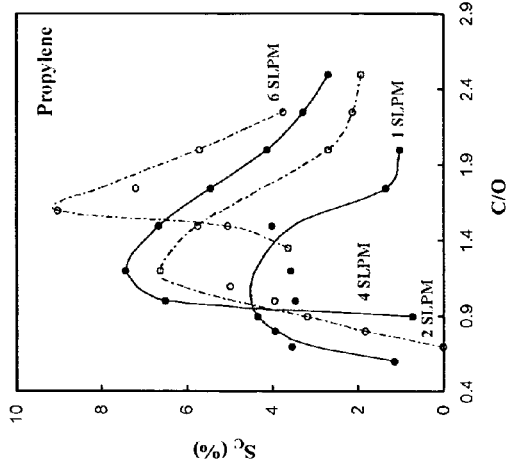
FIG. 10 is an illustrative graphical representation of the product selectivity of propylene obtained from reaction of biodiesel fuel with oxygen at flow rates of 1, 2, 4, and 6 SLPM over a rhodium/cerium catalyst and plotted with respect to the carbon to oxygen ratios used.
Figure 11:
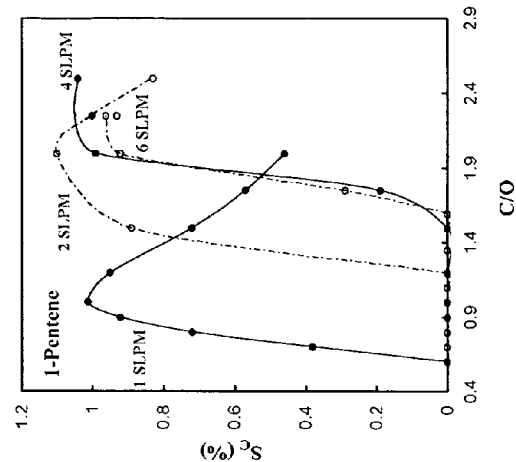
FIG. 11 is an illustrative graphical representation of the product selectivity of 1-pentene obtained from reaction of biodiesel fuel with oxygen at flow rates of 1, 2, 4, and 6 SLPM over a rhodium/cerium catalyst and plotted with respect to the carbon to oxygen ratios used.
Figure 8:
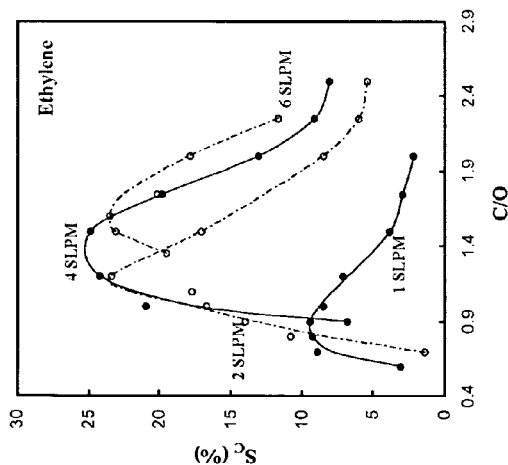
FIG. 8 is an illustrative graphical representation of the product selectivity of ethylene obtained from reaction of biodiesel fuel with oxygen at flow rates of 1, 2, 4, and 6 SLPM over a rhodium/cerium catalyst and plotted with respect to the carbon to oxygen ratios used.
Figure 9:
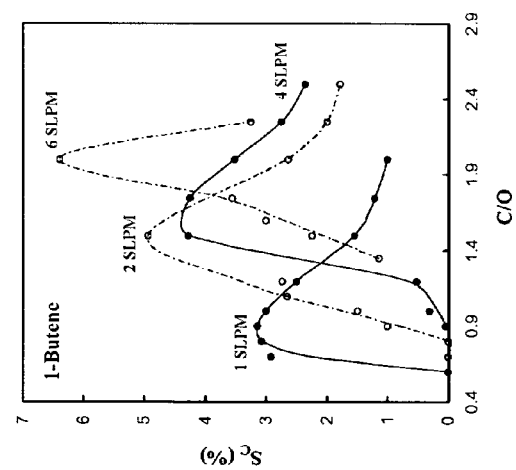
FIG. 9 is an illustrative graphical representation of the product selectivity of 1-butene obtained from reaction of biodiesel fuel with oxygen at flow rates of 1, 2, 4, and 6 SLPM over a rhodium/cerium catalyst and plotted with respect to the carbon to oxygen ratios used.

A graph of the conversion percentages of the biodiesel fuel and the oxygen that was observed in the reaction of biodiesel fuel with oxygen at flow rates of 1, 2, 4, and 6 SLPM over a rhodium/cerium catalyst and plotted with respect to the carbon to oxygen ratios used is also shown. FIG. 2 shows the biodiesel fuel conversion and FIG. 3 shows the oxygen conversion.

Graphs of the product selectivities of hydrogen, water, carbon monoxide, and carbon dioxide, in FIGS. 4, 5, 6, and 7, respectively, which were obtained from reaction of biodiesel fuel with oxygen at flow rates of 1, 2, 4, and 6 standard liters per minute (SLPM) over a rhodium/cerium catalyst and plotted with respect to the carbon to oxygen ratios used are provided.

Graphs of the product selectivities of ethylene, 1-butene, propylene, and 1-pentene, in FIGS. 8, 9, 10, and 11, respectively, which were obtained from the above reactions of biodiesel fuel with oxygen at flow rates of 1, 2, 4, and 6 SLPM over a rhodium/cerium catalyst and plotted with respect to the carbon to oxygen ratios used are provided.

Figure 12:
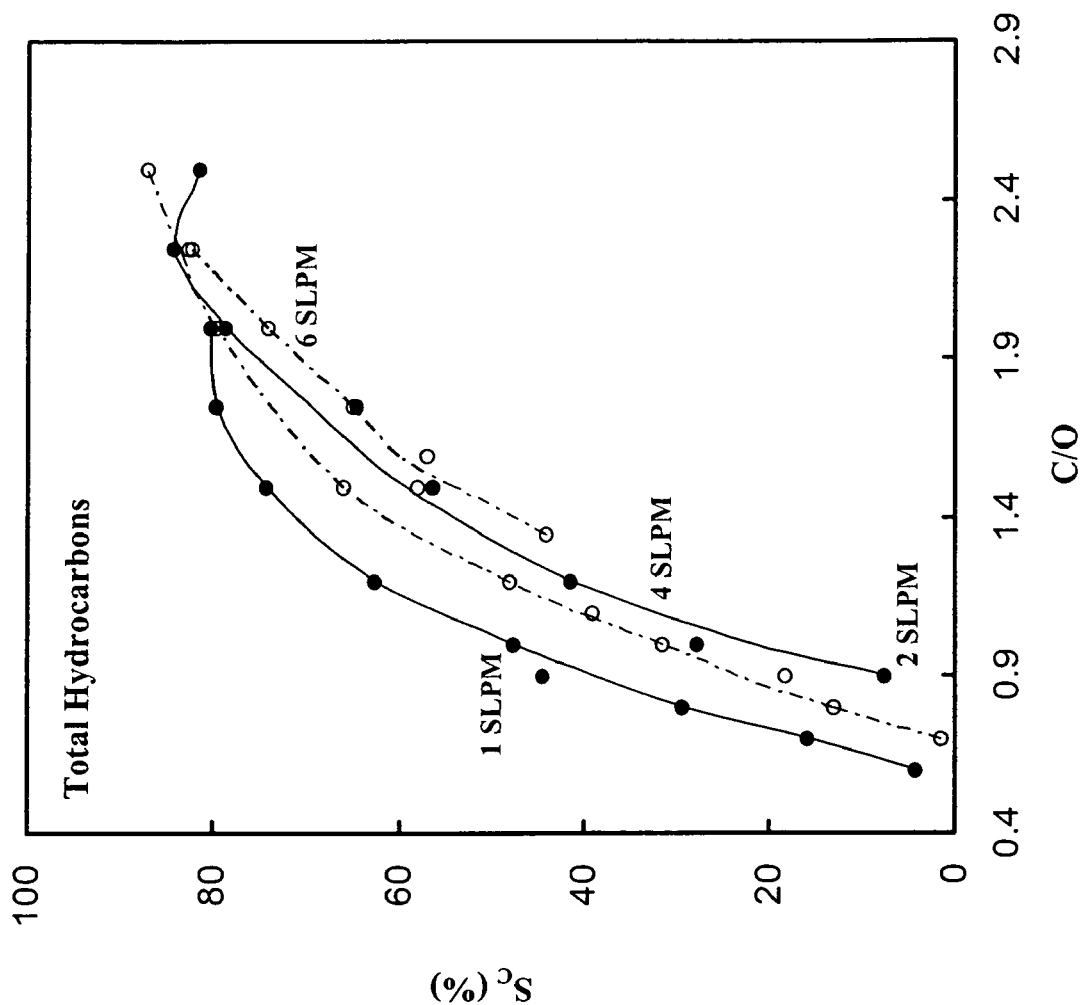
FIG. 12 is an illustrative graphical representation of the selectivities to "total hydrocarbons" obtained from reaction of biodiesel fuel with oxygen at flow rates of 1, 2, 4, and 6 SLPM over a rhodium/cerium catalyst and plotted with respect to the carbon to oxygen ratios used.
Figure 14:
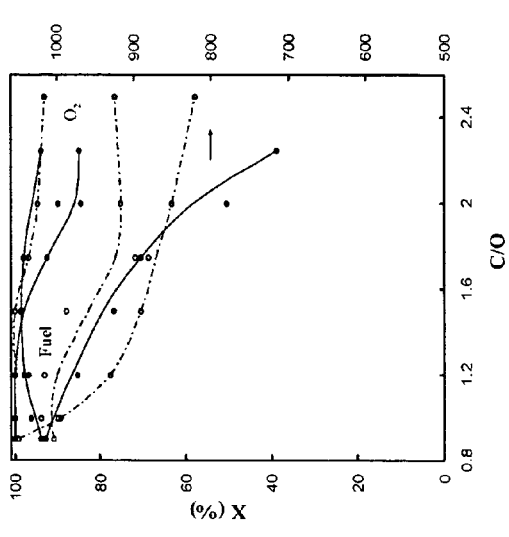
FIG. 14 is an illustrative graphical representation of reactor temperatures and conversion percentages for the reaction of biodiesel fuel with oxygen and reaction of hexadecane with oxygen at a flow rates of 4 SLPM over a rhodium/cerium catalyst and plotted with respect to the carbon to oxygen ratios used.
Figure 16:
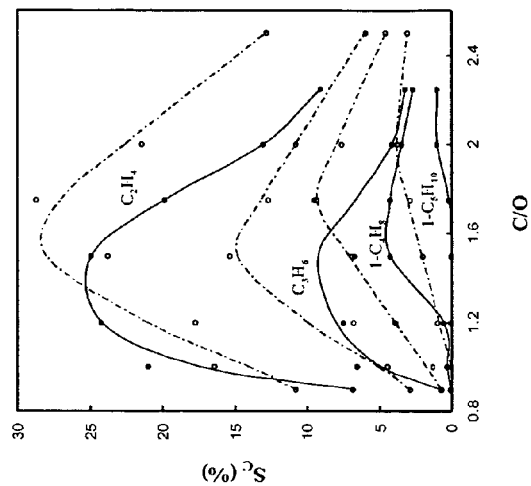
FIG. 16 is an illustrative graphical representation of the product selectivities of ethylene, propylene, 1-butene, and 1-pentene obtained from reaction of biodiesel fuel with oxygen and reaction of hexadecane with oxygen at a flow rate of 4 SLPM over a rhodium/cerium catalyst and plotted with respect to the carbon to oxygen ratios used.

FIG. 12 provides the selectivities to "total hydrocarbons" obtained from reaction of biodiesel fuel with oxygen at flow rates of 1, 2, 4, and 6 SLPM over the rhodium/cerium catalyst respect to the C/O ratio. The term "total hydrocarbons" used herein is understood to refer to all hydrocarbon products having a carbon chain length of $C_2$ through $C_{15}$. Species having a carbon chain length from about 2 to about 5 were typically exclusively olefins, and larger species, also referred to herein as "higher hydrocarbons," included olefins, functionalized olefins, and olefinic esters.

The lower limit, about 0.6, was set by the maximum temperatures that the catalyst was believed to be able to withstand without metal loss. Therefore C/O ratios of less than about 0.6 were seldom used. The upper C/O limit was selected according to the extinguishing of the autothermal reaction. That is, the reactor no longer operates under the conditions of the present invention when the C/O ratio exceeds about 2.5. The fuel flow rate and the C/O ratio used determine the reactor temperature, and low reactor temperatures it was found result in low conversion. Therefore, although the process performs at C/O ratios higher than about 2.5, high C/O ratio processes that extinguished the reaction were not preferred.

Comparison with N-Hexadecane

As biodiesel contains $C_{16}$ and $C_{18}$ fatty acids, its molecular weight and isomers are expected to correspond closely to hexadecane. As a comparison, the above examples were repeated.

Figure 13:
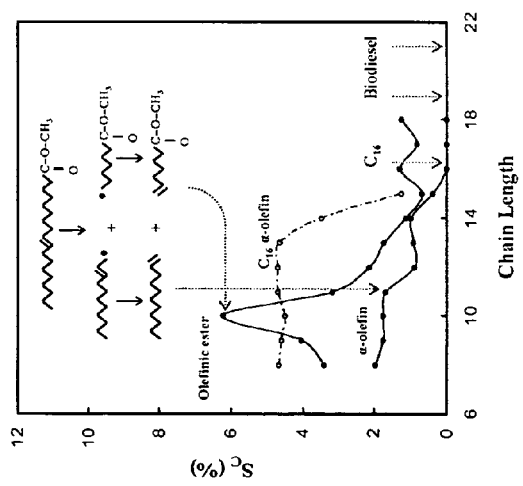
FIG. 13 is an illustrative graphical representation of selectivities for different species versus the chain length of the products observed at C/O=2.25 and a total flow rate of 4 SLPM.

As shown in FIG. 13, about 90% of the molecules present in biodiesel have a double bond between the ninth and tenth carbon atoms. Dissociation occurs mostly near this double bond, because the allylic radical formed is resonance stabilized and this leads to a large amount of olefinic ester with a chain length of 10. In contrast, hexadecane undergoes random C—C scission, leading to nearly equal amounts of all α-olefins up to $C_{14}$.

Figure 15:
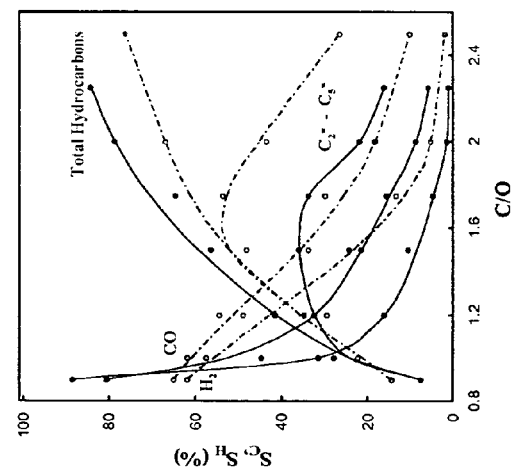
FIG. 15 is an illustrative graphical representation of the product selectivities of hydrogen, carbon monoxide, small olefins ($C_2$ through $C_5$), and "total hydrocarbons" obtained from reaction of biodiesel fuel with oxygen and reaction of hexadecane with oxygen at a flow rate of 4 SLPM over a rhodium/cerium catalyst and plotted with respect to the carbon to oxygen ratios used.

As shown, conversions and selectivities correspond closely between biodiesel and hexadecane. In FIGS. 13 to 16, closed symbols and solid curves represent biodiesel, whereas open symbols and dotted lines indicate hexadecane. For a flow rate of 4 SLPM using hexadecane, with catalyst backface temperatures, fuel and oxygen conversions, product selectivities and olefin selectivities shown in FIGS. 13 and 14. FIG. 15 also show the values obtained at a flow rate of 4 SLPM for biodiesel, to provide a comparison.

Also, the amounts of hydrocarbon products are roughly comparable from biodiesel and n-hexadecane. The results show that the total hydrocarbon products are approximately 10% higher with biodiesel at all indicated C/O ratios. The results further show that there are slightly fewer $C_2$ to $C_5$ olefins from biodiesel at many C/O ratios. However, these results are believed to be a strong function of the catalyst temperature, which varies between fuels.

The results further show that one difference between reaction of biodiesel and reaction of hexadecane is in the chain length of product obtained at different C/O ratios. Mass spectrometry indicated both α-olefins and olefinic esters from biodiesel, but only α-olefins from hexadecane. FIG. 13 shows plots of selectivities for different species versus the chain length of the products. These were obtained from GC peak areas calibrated against reactants and standards. For n-hexadecane, the selectivity to each olefin is about 5% from $C_8$ to $C_{13}$, and it falls to about 3% at $C_{14}$ and to about 1% at $C_{15}$. For biodiesel, the α-olefin peaks lined up with those from n-hexadecane with selectivities of about 1% to about 2% for each species. The olefinic ester peaks are much larger, peaking at about 6% at a chain length of 10. The GC spectrum of biodiesel was much more complicated than that of n-hexadecane, and approximately 20% of all species with chain length greater than 7 could not be identified with either olefin or olefinic ester.

Reaction Mechanisms

Without being held to any particular theory, it is believed that the processes of the present invention are initiated by surface oxidation reactions on the catalyst surface that produces primarily $H_2$, $H_2O$, $CO$, and $CO_2$. These reactions typically occur near the entrance of the catalyst where the surface is nearly free of carbon (Krummenacher et al., *J. Catal.*, 215:332 (2003)).

It is further believed that most or substantially all of the other reaction products, including olefins and olefinic esters, arise from homogeneous reactions that occur after most of the oxygen has been consumed (Krummenacher et al., *J. Catal.*, 215:332 (2003)). As biodiesel may contain both carboxylate groups and up to three carbon-carbon double bonds, it would be expected to find considerable differences and greater complexity in the reaction products formed from biodiesel as compared with saturated alkanes.

Deactivation of the catalyst or extinction of the reaction were not observed in the examples up to a carbon to oxygen ratio of 2, which is believed to indicate that carbon in the catalyst was not formed in sufficient quantities to block catalyst surface sites required for oxidation reactions. Further in the catalyst it is believed that catalyst sites are carbon covered (up to about 5% carbon by weight of the monolith), but this is believed to not cause time-dependent results, so a steady state is rapidly obtained. Further in the catalyst, carbon may prevent further surface reactions thus allowing homogeneous reactions to proceed with the monolith only supplying heat to maintain the reactant temperatures.

For n-hexadecane the reaction is quantitatively fit assuming a very simple mechanism of dissociation of the parent molecule into two radicals:

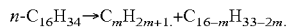

followed by the elimination of the H atom on the carbon atom in the position β to the radical:

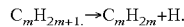

to produce the corresponding α-olefins. The alternative to β-H elimination is β-scission of a C—C double bond:

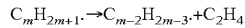

which produces ethylene and a smaller alkyl radical. This reaction can continue producing ethylene until the final radical is ethyl or propyl, which dehydrogenates to form ethylene or propylene. Since β-H elimination has a lower activation energy than elimination of the alkyl to form ethylene, it is believed that a higher reaction temperature (lower C:O ratio) favors the production of smaller olefins and, conversely, lower reaction temperatures favors the production of larger olefins, as is shown in the above examples.

Biodiesel is more complex than n-hexadecane because of the presence of the ester and because there is typically at least one carbon-carbon double bond present in approximately 90% of the molecules present in biodiesel. It is believed that, as carbon-carbon double bonds and carbon-oxygen bonds are stronger than carbon-carbon single bonds, dissociation of the molecule should occur mostly at carbon-carbon single bonds. It is believed that the most likely carbon-carbon single bond dissociation occurs where the activation energy is lowest, which is where the allylic radical stabilizes one of the radicals as a resonance structure, $R=C-C$. and $R-C=C$.

Since in soy oil the first carbon-carbon double bond always occurs between the ninth and tenth carbon atoms in the fatty acid chain (counting the carbon on the carbonyl as carbon 1), the most likely dissociation location in approximately 90% of the biodiesel molecules is expected to occur between the eighth and ninth carbon atoms, as shown by the above results.

From these radicals, the ester radical is expected to undergo β-H elimination to produce the olefinic ester with a chain length of 10. The allylic radical is expected to eliminate H to form an α-olefin with 11 carbon atoms.

According to the above, it is predicted that the dominant olefinic ester is expected to have a chain length of 10, which is observed by maximum selectivity observed in the above results. There are few olefins having greater than 11 carbons (less than 1% selectivity).

Direct Conversion of Soy Oil

Figure 18:
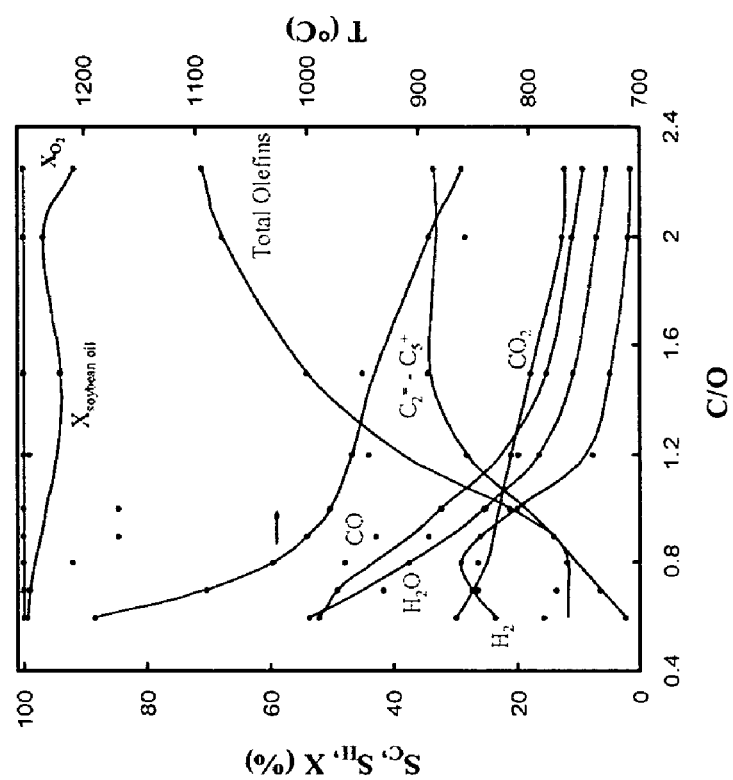
FIG. 18 is an illustrative graphical representation of fuel and oxygen conversions, reactor temperature and product selectivities of hydrogen, carbon monoxide, water, carbon dioxide, small olefins ($C_2$ through $C_5$), and "total olefins" obtained from reaction of soy oil with oxygen at a flow rate of 4 SLPM over a rhodium/cerium catalyst and plotted with respect to the carbon to oxygen ratios used.
Figure 17:
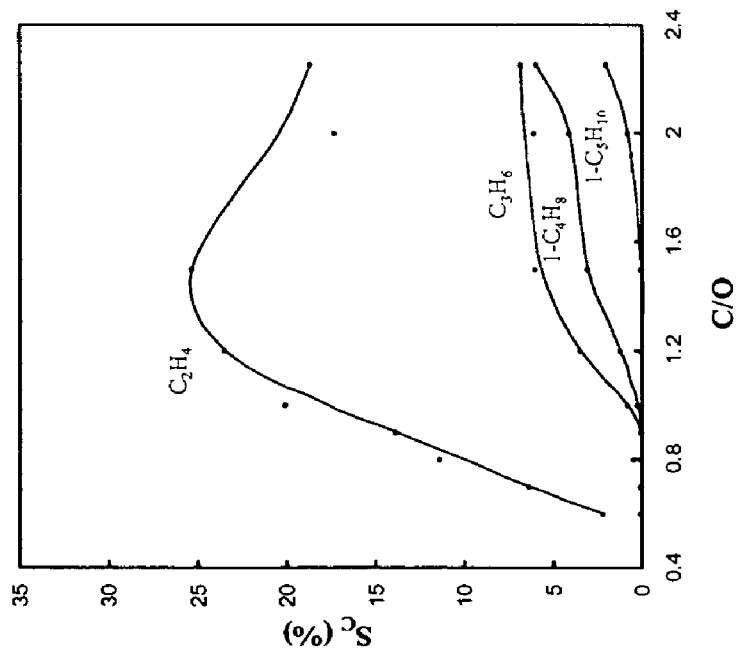
FIG. 17 is an illustrative graphical representation of the product selectivities of ethylene, propylene, 1-butene, and 1-pentene obtained from reaction of soy oil with oxygen at a flow rate of 4 SLPM over a rhodium/cerium catalyst and plotted with respect to the carbon to oxygen ratios used.

Soy oil, from which biodiesel may be derived, was also reacted in the above apparatus. It was found that the reactor could be operated successfully for over 20 hours without forming excessive carbon in the reactor and without deactivating the catalyst. Selectivities of up to about 35% $C_2$ to $C_5$ olefins and up to 70% total hydrocarbons were obtained by direct conversion of the soy oil (FIGS. 17 and 18).

The complete disclosure of any and all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A process for the production of an organic compound, the process comprising:
   providing a catalyst for a partial oxidation and/or steam cracking process;
   providing a fuel source to a reactor, wherein the fuel source comprises at least one organic compound comprising a functional group; and
   providing at least one source of oxygen to the reactor;
   wherein the process comprises conditions effective to produce a partial oxidation and/or steam cracking reaction product comprising an olefin comprising the functional group, wherein the reaction temperature is at least about 600° C., and wherein the olefin comprising the functional group is not present in the fuel source.

2. The process of claim 1 wherein the at least one organic compound comprises at least 2 functional groups.

3. The process of claim 1 wherein the functional group is selected from the group consisting of an alcohol, an aldehyde, a carboxylic acid, a carboxylic acid ester, a ketone, an acid halide, an amide, an ether, an alkyl halide, and combinations thereof.

4. A process for the production of an organic compound, the process comprising:
providing a catalyst for a partial oxidation and/or steam cracking process;
providing a fuel source to a reactor, wherein the fuel source comprises at least one organic compound comprising a functional group; and
providing at least one source of oxygen to the reactor;
wherein the process comprises conditions effective to produce a partial oxidation and/or steam cracking reaction product comprising a non-functionalized olefin and an olefin comprising the functional group, wherein the olefin comprising the functional group is not present in the fuel source.

5. The process of claim 1 wherein the reaction product comprises compounds selected from the group consisting of olefins, functionalized olefins, dienes, functionalized dienes, polyenes, functionalized polyenes, and combinations thereof.

6. The process of claim 1 wherein the fuel source comprises at least one biofeedstock.

7. The process of claim 6 wherein the biofeedstock comprises at least one compound selected from the group consisting of carbohydrates, triglycerides, polyols, and combinations thereof.

8. The process of claim 7 wherein the triglycerides are selected from the group consisting of vegetable oil, animal fat, animal oil, and combinations thereof.

9. The process of claim 8 wherein the vegetable oil is selected from the group consisting of soy oil, palm oil, olive oil, sunflower seed oil, safflower seed oil, rape seed oil, wheat germ oil, corn oil, peanut oil, canola oil, grapeseed oil, castor oil, coconut oil, and combinations thereof.

10. The process of claim 6 wherein the functional group is a methyl carboxylic acid ester.

11. The process of claim 6 wherein the functional group is an ethyl carboxylic acid ester.

12. The process of claim 6 wherein the functional group is a higher alcohol carboxylic acid ester.

13. A process for the production of an organic compound, the process comprising:
providing a catalyst;
providing a fuel source to a reactor, wherein the fuel source comprises at least one organic compound comprising a functional group; and
providing at least one source of oxygen to the reactor;
wherein the process comprises conditions effective to produce a reaction product comprising an olefin comprising the functional group, wherein the reaction temperature is at least about 600° C., wherein the olefin comprising the functional group is not present in the fuel source, wherein the fuel source comprises at least one biofeedstock, and wherein the biofeedstock comprises biodiesel.

14. The process of claim 1 wherein the catalyst comprises a metal disposed on a support, wherein the metal is selected from the group consisting of a Group VIII metal, a Group IB metal, tin, and combinations thereof.

15. The process of claim 14 wherein the metal is selected from the group consisting of rhodium, platinum, and combinations thereof.

16. The process of claim 14 wherein the catalyst further comprises at least one metal selected from the group consisting of Ce, Pd, Pt, Ru, Ir, Os, Mg, Cu, Si, Ti, V, Zn, La, Sm, Zr, Hf, Cr, Mn, Fe, Co, Ni, Cu, Y, Sn, Sb, Re, Eu, Yb, and combinations thereof.

17. The process of claim 14 wherein the metal comprises a pure metal, a metal oxide, a metal alloy, or combinations thereof.

18. The process of claim 14 wherein the catalyst comprises a support selected from the group consisting of metal monolith, metal foam, ceramic monolith, foam ceramic monolith, solid spheres, porous spheres, pellets, gauze, wires, plates, and combinations thereof.

19. The process of claim 1 wherein the catalyst is present in a reactor selected from the group consisting of an autothermal reactor, a fluidized bed reactor, a packed bed reactor, a catalytic wall reactor, a riser reactor, and combinations thereof.

20. The process of claim 1 wherein the source of oxygen is selected from the group consisting of air, $O_2$, oxygen-enriched gas, and combinations thereof.

21. A process for the production of an organic compound, the process comprising:
providing a catalyst for a partial oxidation and/or steam cracking process;
providing a fuel source to a reactor, wherein the fuel source comprises at least one organic compound comprising a functional group; and
providing at least one source of oxygen to the reactor;
wherein the process comprises conditions effective to produce a partial oxidation and/or steam cracking reaction product comprising synthesis gas and an olefin comprising the functional group, wherein the reaction temperature is at least about 600° C., and wherein the olefin comprising the functional group is not present in the fuel source.

22. The process of claim 1 wherein the overall process is carried out under autothermal conditions.

23. The process of claim 1 further comprising an inert carrier gas.

24. The process of claim 23 wherein the inert carrier gas is selected from the group consisting of nitrogen, argon, helium, and combinations thereof.

25. The process of claim 1 further comprising contacting the fuel source and the source of oxygen with water.

26. A process for the production of a reaction product comprising at least one olefinic ester, the process comprising:
providing a reactor comprising a catalyst for a partial oxidation and/or steam cracking process;
providing a fuel source comprising a biofeedstock comprising at least one organic compound comprising an ester functional group;
providing at least one source of oxygen;
delivering the fuel source to the reactor;
delivering the source of oxygen to the reactor;
mixing the fuel source and the source of oxygen to provide a fuel and oxygen mixture; and
contacting the fuel and oxygen mixture with the catalyst under conditions effective to provide a partial oxidation and/or steam cracking reaction product comprising at least one olefinic ester not present in the fuel source, wherein the reaction temperature is at least about 600° C.

27. A process for the production of a reaction product comprising at least one olefinic ester, the process comprising:
providing a reactor comprising a catalyst for a partial oxidation and/or steam cracking process;
providing a fuel source comprising a biofeedstock comprising at least one organic compound comprising an ester functional group;

providing at least one source of oxygen;
delivering the fuel source to the reactor;
delivering the source of oxygen to the reactor;
mixing the fuel source and the source of oxygen to provide a fuel and oxygen mixture; and
contacting the fuel and oxygen mixture with the catalyst under conditions effective to provide a partial oxidation and/or steam cracking reaction product comprising at least one non-functionalized olefin and at least one olefinic ester not present in the fuel source.

28. The process of claim 27 wherein the non-functionalized olefin is ethylene.

29. The process of claim 27 wherein the non-functionalized olefin is propylene.

30. The process of claim 29 wherein the fuel source is a liquid fuel source and further wherein the liquid fuel source is vaporized prior to mixing with the source of oxygen.

31. The process of claim 30 wherein the liquid fuel source is vaporized and mixed with the oxygen source substantially simultaneously.

32. The process of claim 26 wherein at least about 20 mole percent of the ester functional group of the provided fuel source is present in the reaction product.

33. The process of claim 32 wherein at least about 50 mole percent of the ester functional group of the provided fuel source is present in the reaction product.

34. The process of claim 33 wherein at least about 75 mole percent of the ester functional group of the provided fuel source is present in the reaction product.

35. The process of claim 26 wherein the fuel and oxygen mixture are contacted with the catalyst for at least about 5 milliseconds.

36. The process of claim 35 wherein the fuel and oxygen mixture are contacted with the catalyst for no greater than about 50 milliseconds.

37. The process of claim 26 wherein the fuel and oxygen mixture, prior to contacting the catalyst, is heated to a temperature of at least about 25° C. above the boiling point of the fuel source.

38. The process of claim 37 wherein the fuel and oxygen mixture, prior to contacting the catalyst, is heated to a temperature of at no greater than about 150° C. above the boiling point of the fuel source.

39. The process of claim 26 wherein the fuel and oxygen mixture are contacted with the catalyst at a flow rate of at least about $1.5 \times 10^5$ $hr^{-1}$ Gas Hourly Space Velocity.

40. The process of claim 39 wherein the fuel and oxygen mixture are contacted with the catalyst at a flow rate of no greater than about $6 \times 10^6$ $hr^{-1}$ Gas Hourly Space Velocity.

41. The process of claim 26 wherein the catalyst comprises a metal disposed on a support, wherein the metal is selected from the group consisting of a Group VIII metal, a Group IB metal, tin, and combinations thereof.

42. The process of claim 41 wherein the metal is selected from the group consisting of rhodium, platinum, and combinations thereof.

43. The process of claim 41 wherein the catalyst further comprises at least one metal selected from the group consisting of Ce, Pd, Pt, Ru, Ir, Os, Mg, Cu, Si, Ti, V, Zn, La, Sm, Zr, Hf, Cr, Mn, Fe, Co, Ni, Cu, Y, Sn, Sb, Re, Eu, Yb, and combinations thereof.

44. The process of claim 26 wherein the carbon to oxygen ratio in the fuel and oxygen mixture is in an atomic ratio of at least about 0.8.

45. The process of claim 44 wherein carbon to oxygen ratio in the fuel and oxygen mixture is in an atomic ratio of no greater than about 5.

46. A process for the production of a reaction product comprising at least one functionalized olefin, the process comprising:
providing a reactor comprising a catalyst for a partial oxidation and/or steam cracking process;
providing a fuel source comprising a biofeedstock comprising at least one organic compound comprising a functional group;
providing at least one source of oxygen;
delivering the fuel source to the reactor;
delivering the source of oxygen to the reactor;
mixing the fuel source and the source of oxygen to provide a fuel and oxygen mixture; and
contacting the fuel and oxygen mixture with the catalyst under conditions effective to provide a partial oxidation and/or steam cracking reaction product comprising at least one non-functionalized olefin and at least one olefin comprising the functional group, wherein the olefin comprising the functional group is not present in the fuel source.

47. The process of claim 46 wherein the non-functionalized olefin is ethylene.

48. The process of claim 46 wherein the non-functionalized olefin is propylene.

49. The process of claim 46 wherein the functional group is selected from the group consisting of an alcohol, an aldehyde, a carboxylic acid, a carboxylic acid ester, a ketone, an acid halide, an amide, an ether, an alkyl halide, and combinations thereof.

50. The process of claim 46 wherein the reaction product comprises compounds selected from the group consisting of olefins, functionalized olefins, dienes, functionalized dienes, polyenes, functionalized polyenes, and combinations thereof.

51. The process of claim 46 wherein the biofeedstock comprises at least one compound selected from the group consisting of carbohydrates, triglycerides, polyols, and combinations thereof.

52. The process of claim 51 wherein the triglycerides are selected from the group consisting of vegetable oil, animal fat, animal oil, and combinations thereof.

53. The process of claim 52 wherein the vegetable oil is selected from the group consisting of soy oil, palm oil, olive oil, sunflower seed oil, safflower seed oil, rape seed oil, wheat germ oil, corn oil, peanut oil, canola oil, grapeseed oil, castor oil, coconut oil, and combinations thereof.

54. The process of claim 46 wherein the biofeedstock comprises biodiesel.

55. The process of claim 46 wherein the catalyst comprises a metal disposed on a support, wherein the metal is selected from the group consisting of a Group VIII metal, a Group IB metal, tin, and combinations thereof.

56. The process of claim 55 wherein the metal is selected from the group consisting of rhodium, platinum, and combinations thereof.

57. The process of claim 56 wherein the catalyst further comprises at least one metal selected from the group consisting of Ce, Pd, Pt, Ru, Ir, Os, Mg, Cu, Si, Ti, V, Zn, La, Sm, Zr, Hf, Cr, Mn, Fe, Co, Ni, Cu, Y, Sn, Sb, Re, Eu, Yb, and combinations thereof.

58. The process of claim 46 wherein the reactor is selected from the group consisting of an autothermal reactor, a fluidized bed reactor, a packed bed reactor, a catalytic wall reactor, a riser reactor, and combinations thereof.

59. The process of claim 46 wherein the source of oxygen is selected from the group consisting of air, $O_2$, oxygen-enriched gas, and combinations thereof.

60. A process for the production of an organic compound, the process comprising:
 providing a catalyst;
 providing a fuel source to a reactor, wherein the fuel source comprises at least one organic compound comprising a functional group; and
 providing at least one source of oxygen to the reactor; wherein the process comprises conditions effective to produce a reaction product comprising an olefin comprising the functional group, wherein the olefin comprising the functional group is not present in the fuel source, wherein the fuel source comprises at least one biofeedstock, and wherein the biofeedstock comprises biodiesel.

* * * * *